(12) United States Patent
Beliard et al.

(10) Patent No.: US 8,685,725 B2
(45) Date of Patent: *Apr. 1, 2014

(54) MONOCLONAL ANTIBODIES WITH ENHANCED ADCC FUNCTION

(75) Inventors: Roland Beliard, Santes (FR);
Dominique Bourel, La Madeleine (FR);
Arnaud Glacet, Gondecourt (FR);
Christophe De Romeuf, Lille (FR);
Nicolas Bihoreau, Orsay (FR);
Emmanuel Nony, Antony (FR)

(73) Assignee: Labortoire Francais du Fractionnement et des Biotechnologies, Les Ulis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/077,644

(22) Filed: Mar. 31, 2011

(65) Prior Publication Data

US 2011/0223658 A1  Sep. 15, 2011

Related U.S. Application Data

(60) Continuation of application No. 11/039,877, filed on Jan. 24, 2005, now Pat. No. 7,931,895, which is a division of application No. 10/257,477, filed as application No. PCT/FR01/01127 on Apr. 12, 2001, now Pat. No. 7,579,170.

(30) Foreign Application Priority Data

Apr. 12, 2000 (FR) .................................... 00 04685

(51) Int. Cl.
C12N 5/00 (2006.01)
C12N 5/16 (2006.01)
C07K 16/00 (2006.01)

(52) U.S. Cl.
USPC .......................................... 435/325; 435/328

(58) Field of Classification Search
None
See application file for complete search history.

(56) References Cited

U.S. PATENT DOCUMENTS

| | | | |
|---|---|---|---|
| 5,830,470 A | 11/1998 | Nakamura et al. | |
| 5,843,708 A | 12/1998 | Hardman et al. | |
| 5,851,524 A | 12/1998 | Byrne et al. | |
| 7,214,775 B2 | 5/2007 | Hanai et al. | |
| 2002/0164328 A1 | 11/2002 | Shinkawa et al. | |
| 2003/0115614 A1 | 6/2003 | Kanda et al. | |

FOREIGN PATENT DOCUMENTS

| | | |
|---|---|---|
| EP | 0 249 557 | 12/1987 |
| EP | 0 251 440 | 1/1988 |
| EP | 0 576 093 | 3/2000 |
| EP | 1 176 195 | 1/2002 |
| EP | 1 229 125 | 8/2002 |
| FR | 2 653 561 | 4/1991 |
| JP | 63-50710 | 3/1988 |
| RU | 2 094 462 C1 | 10/1997 |
| WO | WO 85/02413 | 6/1985 |
| WO | WO-89/02442 | 3/1989 |
| WO | WO-89/02600 | 3/1989 |
| WO | WO 99/54342 | 10/1999 |
| WO | WO 00/61739 | 10/2000 |
| WO | WO 01/29246 | 4/2001 |
| WO | WO 02/30954 | 4/2002 |
| WO | WO 02/31140 | 4/2002 |
| WO | WO 03/055993 | 7/2003 |
| WO | WO 03/084569 | 10/2003 |
| WO | WO 03/084570 | 10/2003 |
| WO | WO 03/085102 | 10/2003 |
| WO | WO 03/085107 | 10/2003 |
| WO | WO 03/085118 | 10/2003 |
| WO | WO 03/085119 | 10/2003 |

OTHER PUBLICATIONS

Ackermann et al. Biotechnology and Bioengineering, 1995, vol. 45, pp. 97-106.*
Tegeline, May 9, 2007, pp. 1-6.*
Shinkawa et al. JBC 2003, vol. 278, No. 5, pp. 3466-3473.*
North et al. JBC 2010, vol. 285, No. 8, pp. 5759-5775.*
Remarks in U.S. Appl. No. 11/039,877 (US Patent 7,931,895). Nov. 26, 2010. pp. 1-13.*
Bihoreau et al., "Combination of capillary electrophoresis and matrix-assisted laser description ionization mass spectrometry for glycosylation analysis fo a human monoclonal anti-Rhesus(D) antibody," Journal of Chromatography B: Biomedical Sciences & Applications, Elsevier Science Publishers, vol. 697, No. 1-2, Sep. 12, 1997, pp. 123-133, XP0004090752, ISSN: 0378-4347.
Bredius et al., "Role of neutrophil Fc-gamma-RIIa (CD32) and Fc-gamma-RIIIb (CD16 polymorphic forms in phagocytosis of human IfG1- and IgG3-opsonized bacteria and erythrocytes," Immunology, vol. 83, No. 4, 1994, pp. 624-630, XP000971450, ISSN: 0019-2805.
Hadley, et al., "The functional activity of Fc.gamma.RII and Fc.gamma.RIII on subsets of human lymphocytes," Immunology, 1992, vol. 76, No. 3, pp. 446-451, XP001015733.
Klein et al., "Human recombinant anti-Rh(D) monoclonal antibodies: Improvement of biological properties by in vitro class-switch," Human Antibodies, vol. 8, No. 1, 1997, pp. 17-25, XP001015726, ISSN: 1093-2607.
Paterson et al., "Variation in IfF1 heavy chain allotype does not contribute to differences in biological activity of two human anti-Rhesus (D) monoclonal antibodies," Immunotechnology, Elsevier Science Publishers BV, vol. 4, No. 1, Jun. 1, 1998, pp. 37-47, XP004127385, ISSN: 13802933.

(Continued)

*Primary Examiner* — Chun Dahle
(74) *Attorney, Agent, or Firm* — Foley & Lardner LLP

(57) ABSTRACT

The invention concerns a method for obtaining and selecting monoclonal antibodies by an ADDC-type test, said antibodies capable of activating type III Fcγ receptors and having a particular glycan structure. The inventive anti-D antibodies can be used for preventing Rhesus isoimmunization in Rh negative persons, in particular for haemolytic disease in a new-born baby of for uses such as idiopathic thrombocytopenic pupura 9ITP.

26 Claims, 11 Drawing Sheets

(56) References Cited

OTHER PUBLICATIONS

Ugen et al., "New recombinant multimer of two fusion proteins, each including part of C4 binding protein; recombinant complement-C4 binding protein and CD4, CD8, CD16, CD35, Rhesus-D, antigen, enzyme or single chain antibody fusion protein multimer for use as a recombinant vaccine or diagnostic," Vaccine, Butterworth Scientific, Guildford, Great Britain, vol. 15, No. 8, Jun. 1, 1997, p. 935, XP004075692, ISSN: 0264-410X.
Umana et al., "Engineered glycoforms of an antineuro-blastoma IgG1 with optimized antibody-dependent cellular cytotoxic activity," *Nature Biotechnology*, vol. 17, pp. 176-180, Feb. 17, 1999.
Gray, "Overview of Protein Expression by Mammalian Cells," *Current Protocols in Protein Science*, Supplement 10, pp. 5.9.1-5.9.18, 1997.
Chen et al., "Production of Recombinant Proteins in Mammalian Cells," *Current Protocols in Protein Science*, Supplement 12, pp. 5.10.1-5.10.41, 1998.
Freshney, "Maintenance of Cell Culture Lines," *Culture of Animal Cells: a Manual of Basic Technique*, pp. 134-135, 1987.
Toneguzzo et al., "Electric Field-Mediated DNA Transfer: Transient and Stable Gene Expression in Human and Mouse Lymphoid Cells," *Molecular and Cellular Biology*, vol. 6, No. 2, pp. 703-706, 1986. *Current Protocols in Protein Science*, Supplement 10, pp. 5.9.1-5.9.18, 1997.
Keen, M.J., "The culture of rat myeloma and rat hybridoma cells in a protein-free medium," Cytotechnology, 1995, 17:193-202.
Lifely et al., "Glycosylation and biological activity of Campath-1H expressed in different cell lines and grown under different culture conditions," Glycobiology, 1995, 5(8):813-822.
Shitara et al., "A new vector for the high level expression of chimeric antibodies in myeloma cells," J. Immun. Methods, 1994, 167:271-278.
Shepard et al., Vox Sang., 1996, 70:157-163.
Siberil et al., Clinical Immunology, 2006, 118:170-179.
Urbaniak et al., Vox Sang. 1984, 46:323-329.
Lown et al., Immunohematology, 1995, 11:4.
ATCC Product Description for YB2/0 CRL-1662 and Material Transfer Agreement, 2003, pp. 1-6.
Boylston, A. W., et al.; "Production of Human IgM Anti-D in Tissue Culture by EB-Virus-transformed Lymphocytes"; Scand. J. Immunol., 12, 355-358, 1980.
Bron, D. et al.; "Production of human monoclonal IgG antibodies against Rhesus (D) antigen"; Proc. Nat. Acad. Sci., vol. 81, pp. 3214-3217, May 1984.
Chouchane, L., et al.; "Molecular characterization of a human anti-Rh(D) antibody with a DH segment encoded by a germ-line sequence"; Eur. J. Biochem; 207:1115-1121 (1992).
Crawford, D. et al.; "Production of Human Monoclonal Antibody to Rhesus D Antigen"; The Lancet; pp. 386-388; Feb. 19, 1983.
Debré, M.; "Feasibility of administering Tegeline at home Restrospective study of the data concerning efficacy, safety and tolerance"; Pressre Med., 33:682-688 (2004).
Doyle, A. et al.; "In vitro Development of Human Monoclonal Antibody-Secreting Plasmacytomas"; Human Immunology; 13:199-209 (1985).
Edelman, L., et al.; "Obtaining a functional recombinant anti-rhesus (D) antibody using the baculovirus-insect cell expression system"; Immunology 91:13-19 (1997).
Foung, S., et al.; "Human Monoclonal Antibodies to RhO(D)"; Vox Sang; 53:44-47 (1987).
Issitt, P.; "Genetics of the Rh blood group system: some current concepts"; Medical Laboratory Sciences; 45:395-404 (1988).
Jefferis, R. et al.; "A comparative study of the N-linked oligosaccharide structures of human IgC subclass proteins"; Biochem. J. (1990) 268. 529-537.
Jefferis, R. et al.; Molecular Definition of Interaction Sites on Human IgG for Fc Receptors (huFcyR); Molecular Immunology, vol. 27, No. 12, pp. 1237-1240 (1990).

Koskimies; "Human Lymphoblastoid Cell Line Producing Specific Antibody against Rh-Antigen D"; Scand. J. Immunol. 11, 73-77, 1980.
Kumpel et al., "Galactosylation of human IgG monoclonal anti-D produced by EBV-transformed By-lymphoblastoid cell lines is dependent on culture method and affects Fc receptor-mediated functional activity," *Hum. Antibod. Hybridomas*, 1994, pp. 143-151, vol. 5. No. 3 and 4.
Kumpel et al., "Human Rh D monoclonal antibodies (BRAD-3 and BRAD-5) cause accelerated clearance of Rh D+red blood cells and suppression of Rh D immunication in Rh D- volunteers," *Blood*, 1995, pp. 1701-1709, vol. 86, American Society of Hematology.
Kumpel et al., "Human Monoclonal anti-D antibodies," British Journal of Haematology, 71:125-129, 1989.
Leatherbarrow, R. et al.; "Effector Functions of a Monoclonal Aglycosylated Mouse IgG2a: Binding and Activation of Complement Component C1 and Interaction with Human Monocyte Fc Receptor"; Molecular Immunology, vol. 22, No. 4, pp. 407-415, 1985.
Little, S. F., et al.; "Passive Protection by Polyclonal Antibodies against *Bacillus anthracis* Infection in Guinea Pigs"; Infection and Immunity, pp. 5171-5175; (1997).
Lomas, C., et al.; "Demonstration of Seven Epitopes on the Rh Antigen D Using Human Monoclonal Anti-D Antibodies and Red Cells from D Categories"; Vox Sang; 57:261-264 (1989).
Lund, J. et al.; "A Protein Structural Change in Aglycosylated IgG3 Correlates with Loss of huFcyR1 and huFcyR111 Binding and/or Activation"; Molecular Immunology, vol. 27, no. 11, pp. 1145-1153 (1990).
Lund et al.., "Control of IgG/Fc Glycosylation: A comparison of Oligosacharides from Chimeric Human/Mouse and Mouse Subclass Immunoglobulin Gs," Molecular Immunology, vol. 30, No. 8, pp. 741-748, 1993.
MA, J. et al.; Immunotherapeutic potential of antibodies produced in plants; Tibtech, vol. 13, pp. 522-527 (Dec. 1995).
McCann-Carter, M. et al.; "The production and evaluation of two human monoclonal anti-D antibodies"; Transfusion Medicine; 3:187-194 (1993).
Melamed, M. et al.; Senescence of a human lymphoblastoid clone producing anti-Rhesus(D); Eur. J. Immunol.; 15:742-746 (1985).
Monica, T. et al.; "Comparative Biochemical Characterization of a Human IgM Produced in Both Ascites and In vitro Cell Culture"; Bio/Technology vol. 11, pp. 512-515; Apr. 11, 1993.
Parekh, R. et al.; "Association of rheumatoid arthritis and primary osteoarthritis with changes in the glycosylation pattern of total serum IgG"; Nature; vol. 316, pp. 452-457; Aug. 1, 1995.
Thomas, A. et al.; "Clearance of Rh D-positive red cells with monoclonial anti-D"; Lancet; 336:1147-1150 (1990).
Ware, R. et al.; "Anti-D: Mechanisms of Action"; Seminars in Hematology, vol. 35, No. 1, suppl. 1, Jan. 1998.
IP, C. Yu et al.; "Structural Characterization of the N-Glycans of a Humanized Anti-CD 18 Murine Immunoglobulin G"; Archives of Biochemistry and Biophystic; vol. 308, No. 2, pp. 387-399; Feb. 1, 1994.
Zupanska, B. et al.; "Phagocytosis of Erythrocytes Sensitized with Known Amounts of IgG1 and IgG3 Anti-Rh Antibodies"; Vox Sang; 53:96-101 (1987).
Rothman, "Antibody-Dependent Cytotoxicity Mediated by Natural Killer Cells is Enhanced by Castanospermine-Induced Alterations of IgC Glycosylation," Molecular Immunology, vol. 26, No. 12, pp. 1113-1123, 1989.
Vitetta et al., "Considering Therapeutic Antibodies," Science, 313:308-309, 2006.
Hutchins et al., "Improved biodistribution, tumor targeting, and reduced immunogenicity in mice with γ4 variant of Campath-1H," PNAS, 92:11980-11984, 1995.
Notice of Allowance issued by the Examiner in U.S. Appl. No. 11/039,877 on Mar. 3, 2011.
Office Action issued by the Examiner in U.S. Appl. No. 11/039,877 on Oct. 27, 2009.
Office Action issued by the Examiner in U.S. Appl. No. 11/039,877 on Apr. 15, 2009.

(56) References Cited

OTHER PUBLICATIONS

Office Action issued by the Examiner in U.S. Appl. No. 11/039,877 on Aug. 26, 2008.
Office Action issued by the Examiner in U.S. Appl. No. 11/039,877 on Nov. 15, 2007.
Office Action issued by the Examiner in U.S. Appl. No. 11/039,877 on Jul. 25, 2007.
Office Action issued by the Examiner in U.S. Appl. No. 11/039,877 on May 7, 2007.
Office Action issued by the Examiner in U.S. Appl. No. 11/039,877 on Jan. 23, 2007.
Office Action issued by the Examiner in U.S. Appl. No. 11/039,877 on Jun. 14, 2006.
Office Action issued by the Examiner in U.S. Appl. No. 11/039,877 on Feb. 13, 2006.
Dougherty et al., "Transgenes and gene suppression: telling us something new?," Current Opinion in Cell Biology, 1995, pp. 399-405, vol. 7.
Fire et al., "Potent and specific genetic interference by double-stranded RNA in *Caenorhabditis elegans*," Nature, Feb. 1998, pp. 806-811, vol. 391.
Misquitta et al., "Targeted disruption of gene function in *Drosophila* by RNA interference (RNA-i): A role for *nautilus* in embryonic somatic muscle formation," Proc. Natl. Acad. Sci. USA, Feb. 1999, pp. 1451-1456, vol. 96.
Mori et al., "Engineering Chinese Hamster Ovary Cells to Maximize Effector Function of Produced Antibodies Using FUT8 siRNA," Biotechnol Bioeng, Dec. 2004, pp. 901-908, vol. 88, No. 7.
Mortensen R.M., "Double Knockouts. Production of Mutant Cell Lines in Cardiovascular Research," Hypertension, J American Heart Assoc., 1993, pp. 646-651, vol. 22.
Palcic et al., "A Bisubstrate Analog Inhibitor for $\alpha(1\rightarrow 2)$-Fucosyltransferase," J Biological Chem., Oct. 1989, pp. 17174-17181, vol. 264, No. 29.
Ruggiero-Lopez et al., "Participation of an endogenous inhibitor of fucosyltransferase activities in the developmental regulation of intestinal fucosylation processes," Biochem. J., 1991, pp. 801-806, vol. 279.
Yamaguchi et al., "Mapping of the $\alpha$-1,6-fucosyltransferase gene, FUT8, to human chromosome 14q24.3," Cytogenet Cell Genet, 1999, pp. 58-60, vol. 84.
Yamane-Ohnuki et al., "Establishment of *FUT8* Knockout Chinese Hamster Ovary Cells: An Ideal Host Cell Line for Producing Completely Defucosylated antibodies With Enhanced Antibody-Dependent Cellular Cytotoxicity," Biotechnol Bioeng, Sep. 2004, pp. 614-622, vol. 87, No. 5.
Ruggiero-Lopez et al., "Effects of Endogenous Soluble galactoside binding lectins and protein inhibitor of fucosyltransferase on the enzymes involved in the intestinal fucosylation process," Biochemical and Biophysical Research Communications, 1992, pp. 617-623, vol. 185.

\* cited by examiner

SEQUENCE LISTING

<160> NUMBER OF SEQ ID NOS: 10

<210> SEQ ID NO 1
<211> LENGTH: 44
<212> TYPE: DNA
<213> ORGANISM: Artificial sequence
<220> FEATURE:
<223> OTHER INFORMATION: Primer A2VH5

<400> SEQUENCE: 1
ctctccgaat tcgccgccac catggagttt gggctgagct gggt        44

<210> SEQ ID NO 2
<211> LENGTH: 23
<212> TYPE: DNA
<213> ORGANISM: Artificial sequence
<220> FEATURE:
<223> OTHER INFORMATION: Antisens primer GSP2ANP

<400> SEQUENCE: 2
ggaagtagtc cttgaccagg cag        23

<210> SEQ ID NO 3
<211> LENGTH: 24
<212> TYPE: DNA
<213> ORGANISM: Artificial sequence
<220> FEATURE:
<223> OTHER INFORMATION: Primer G1

<400> SEQUENCE: 3
ccctccacca agggcccatc ggtc        24

<210> SEQ ID NO 4
<211> LENGTH: 36
<212> TYPE: DNA
<213> ORGANISM: Artificial sequence
<220> FEATURE:
<223> OTHER INFORMATION: Antisens primer H3'Xba

<400> SEQUENCE: 4
gagaggtcta gactatttac ccggagacag ggagag        36

```
<210> SEQ ID NO 5
<211> LENGTH: 44
<212> TYPE: DNA
<213> ORGANISM: Artificial sequence
<220> FEATURE:
<223> OTHER INFORMATION: Primer A2VK3

<400> SEQUENCE: 5
cctaccgaat cgccgccac catggacatg agggtccccg ctca            44

<210> SEQ ID NO 6
<211> LENGTH: 39
<212> TYPE: DNA
<213> ORGANISM: Artificial sequence
<220> FEATURE:
<223> OTHER INFORMATION: Antisens primer KSE1

<400> SEQUENCE: 6
ggtggtgaat tcctaacact ctcccctgtt gaagctctt                 39

<210> SEQ ID NO 7
<211> LENGTH: 42
<212> TYPE: DNA
<213> ORGANISM: Artificial sequence
<220> FEATURE:
<223> OTHER INFORMATION: Primer A2VK9

<400> SEQUENCE: 7
cctaccgaat cgccgccac catgagggtc cccgctcagc tc              42

<210> SEQ ID NO 8
<211> LENGTH: 55
<212> TYPE: DNA
<213> ORGANISM: Artificial sequence
<220> FEATURE:
<223> OTHER INFORMATION: Primer DF5VH1

<400> SEQUENCE: 8
ctctccgaat cgccgccac catggactgg acctggagga tcctcttttt ggtgg    55

<210> SEQ ID NO 9
<211> LENGTH: 47
<212> TYPE: DNA
<213> ORGANISM: Artificial sequence
<220> FEATURE:
<223> OTHER INFORMATION: Primer DF5VLBD1

<400> SEQUENCE: 9
cctaccgaat cgccgccac catggcctgg tctcctctcc tcctcac         47

<210> SEQ ID NO 10
<211> LENGTH: 43
<212> TYPE: DNA
<213> ORGANISM: Artificial sequence
<220> FEATURE:
<223> OTHER INFORMATION: Antisens primer LSE1

<400> SEQUENCE: 10
gaggaggaat tcactatgaa cattctgtag gggccactgt ctt            43
```

MONOCLONAL ANTIBODIES WITH ENHANCED ADCC FUNCTION

CROSS-REFERENCE TO RELATED PATENT APPLICATIONS

This application a continuation of U.S. application Ser. No. 11/039,877, filed Jan. 24, 2005, now U.S. Pat. No. 7,931,895, which is a divisional of U.S. application Ser. No. 10/257,477, filed Jan. 14, 2003, now U.S. Pat. No. 7,579,170, which is a U.S. National Stage of International application serial number PCT/FR01/01127, filed Apr. 12, 2001, which claims priority to France application serial number 00/04,685, filed Apr. 12, 2000, all of which are incorporated herein by reference in their entirety.

BACKGROUND OF THE INVENTION

The present invention relates to a method of obtaining and selecting monoclonal antibodies using an assay of the ADCC type, said antibodies being capable of activating Fcγ type III receptors. The invention is also directed toward monoclonal antibodies having a particular glycan structure, the cells producing said antibodies, the methods for preparing the producer cells, and also the pharmaceutical compositions or the diagnostic tests comprising said antibodies. The anti-D antibodies according to the invention can be used for preventing Rhesus isoimmunization of Rh-negative individuals, in particular a hemolytic disease of the newborn (HDN), or in applications such as Idiopathic Thrombocytopenic Purpura (ITP).

Passive immunotherapy using polyclonal antibodies has been carried out since the 1970s. However, the production of polyclonal immunoglobulins poses a problem: The immunization of volunteers was discontinued in France in 1997 because of the ethical problems that such acts present. In France, as in Europe, the number of immunized donors is too low to ensure a sufficient supply of certain antibodies, to such an extent that it proves necessary to import hyperimmunized plasma from the United States for example.

Thus, this immunoglobulin shortage does not make it possible to envisage antenatal administration for preventing HDN.

Various studies have resulted in the production of human monoclonal antibodies for the purpose of replacing the polyclonal antibodies obtained from fractionating plasmas from voluntary donors.

Monoclonal antibodies have several advantages: they can be obtained in large amounts at reasonable costs, each batch of antibodies is homogeneous and the quality of the various batches is reproducible since they are produced by the same cell line, which is cryopreserved in liquid nitrogen. It is possible to ensure the safety of the product with regard to an absence of viral contamination.

Several publications describe the production of cell lines producing human anti-Rh D monoclonal antibodies of IgG class, from B cells of immunized donors. Boylston et al. 1980; Koskimies 1980; Crawford et al. 1983; Doyle et al. 1985; Goossens et al. 1987; Kumpel et al. 1989(a) and McCann-Carter et al. 1993 describe the production of B lymphocyte lines transformed with the EBV virus. Melamed et al. 1985; Thompson et al. 1986 and McCann-Carter et al. 1993 relate to heterohybridomas resulting from B lymphocyte (transformed with EBV)×murine myeloma fusion. Goossens et al., 1987 relates to heterohybrids resulting from B lymphocyte (transformed with EBV)×human myeloma fusion. Bron et al., 1984 and Foung et al., 1987 describe heterohybrids resulting from B lymphocyte (transformed with EBV)×human-mouse heteromyeloma fusion and, finally, Edelman et al., 1997 relates to insect cells transfected with the gene encoding an anti-Rh(D) using the baculovirus system.

Among the patents and patent applications relating to such monoclonal antibodies and the lines secreting them, mention may be made of: EP 576093 (AETS (FR), Biotest Pharma GmbH (Germany); Composition for prophylaxis of the haemolytic disease of the new-born comprises two human monoclonal antibodies of sub-class IgG1 and IgG3, which are active against the Rhesus D antigen), RU 2094462, WO 85/02413 (Board of Trustees of the Leland Stanford Jr. University, Human Monoclonal Antibody against Rh (D) antigen and its uses), GB 86-10106 (Central Blood Laboratories Authority, Production of heterohybridomas for manufacture of human monoclonal antibodies to Rhesus D antigen), EP 0 251 440 (Central Blood Laboratories Authority, Human Anti-Rhesus D Producing Heterohybridomas), WO 89/02442, WO 89/02600 and WO 89/024443 (Central Blood Laboratories Authority, Human Anti-Rh (D) Monoclonal Antibodies), WO 8607740 (Institut Pasteur, Protein Performance SA, Paris, FR, Production of a recombinant monoclonal antibody from a human anti-rhesus D monoclonal antibody, production thereof in insect cells and uses thereof), JP 88-50710 (International Reagents Corp., Japan, Reagents for Determination of Blood Group Substance Rh (D) Factor), JP 83-248865 (Mitsubishi Chemical Industries Co., Ltd., Japan, Preparation of Monoclonal Antibody to Rh (D) positive Antigen); CA 82-406033 (Queens University at Kingston, Human Monoclonal Antibodies) and GB 8226513 (University College London, Human Monoclonal Antibody against Rhesus D Antigen).

While the use of monoclonal antibodies has many advantages compared to the use of pools of polyclonal antibodies, it may, on the other hand, prove to be difficult to obtain an effective monoclonal antibody. In fact, it has been found, in the context of the invention, that the Fcγ fragment of the immunoglobulin obtained must have very particular properties in order to be able to interact with and activate the receptors of effector cells (macrophage, TH lymphocyte and NK).

The biological activity of certain G immunoglobulins is dependent on the structure of the oligosaccharides present on the molecule, and in particular on its Fc component. IgG molecules of all human and murine subclasses have an N-oligosaccharide attached to the $CH_2$ domain of each heavy chain (at residue Asn 297 for human IgGs). The influence of this glycan-containing residue on the ability of the antibody to interact with effector molecules (Fc receptors and complement) has been demonstrated Inhibiting glycosylation of a human IgG1, by culturing in the presence of tunicamycin, causes, for example, a 50-fold decrease in the affinity of this antibody for the FcγRI receptor present on monocytes and macrophages (Leatherbarrow et al., 1985). Binding to the FcγRIII receptor is also affected by the loss of carbohydrates on IgG, since it has been described that a nonglycosylated IgG3 is incapable of inducing lysis of the ADCC type via the FcγRIII receptor of NK cells (Lund et al., 1990).

However, beyond the necessary presence of these glycan-containing residues, it is more precisely the heterogeneity of their structure which may result in differences in the ability to initiate effector functions. Galactosylation profiles which are variable depending on individuals (human serum IgG1s) have been observed. These differences probably reflect differences in the activity of galactosyltransferases and other enzymes between the cellular clones of these individuals (Jefferis et al., 1990). Although this normal heterogeneity of post-translational processes generates various glycoforms (even in the case of monoclonal antibodies), it may lead to atypical structures associated with certain pathological conditions, such as rheumatoid arthritis or Crohn's disease, for which a considerable proportion of agalactosylated residues have been demonstrated (Parekh et al., 1985).

The glycosylation profile of the purified molecule is the consequence of multiple effects, some parameters of which have already been studied. The protein backbone of IgGs, and in particular amino acids in contact with the terminal N-acetylglucosamine (GlcNAc) and galactose residues of the mannose α-1,6 arm (aa 246 and 258 of IgGs), may explain the existence of preferential structures (galactosylation), as shown in the study carried out on murine and chimeric IgGs of different isotypes (Lund et al., 1993).

The differences observed also reveal specificities related to the species and to the cell type used for producing the molecule. Thus, the conventional structure of the N-glycans of human IgGs reveals a significant proportion of bi-antennary types with a GlcNAc residue in the bisecting position, this being a structure which is absent in antibodies produced by murine cells. Similarly, the sialic acid residues synthesized by the CHO (Chinese Hamster Ovary) line are exclusively of the α-2,3 type, whereas they are of the α-2,3 and α-2,6 type with murine and human cells (Yu Ip et al., 1994). Immunoglobulin production in expression systems other than those derived from mammals may introduce much more important modifications, such as the presence of xylose residues produced by insect cells or plants (Ma et al., 1995).

Other factors, such as the cell culture conditions (including the composition of the culture medium, the cell density, the pH, the oxygenation), appear to have an effect on glycosyltransferase activity in the cell and, consequently, on the glycan structure of the molecule (Monica et al., 1993; Kumpel et al., 1994 b).

Now, in the context of the present invention, it has been found that a structure of the bi-antennary type, with short chains, a low degree of sialylation, and nonintercalated terminal mannoses and/or terminal GlcNAcs, is the common denominator for glycan structures which confer strong ADCC activity on monoclonal antibodies. A method for preparing such antibodies capable of activating effector cells via FcγRIII, in particular anti-Rh(D) antibodies, has also been developed.

Blood group antigens are classified in several systems depending on the nature of the membrane-bound molecules expressed at the surface of red blood cells. The Rhesus (Rh) system comprises 5 molecules or antigens: D, C, c, E and e (ISSITT, 1988). The D antigen is the most important of these molecules because it is the most immunogenic, i.e. it can induce the production of anti-D antibodies if Rh-D-positive red blood cells are transfused into Rh-negative individuals.

The D antigen is normally expressed in 85% of Caucasian individuals, these people are termed "Rh-positive;" 25% of these individuals are therefore Rh-negative, i.e. their red blood cells do not exhibit any D antigen. D antigen expression exhibits certain variants which may be linked either to a weak antigenic density, reference is then made to weak D antigens, or to a different or partial antigenicity, reference is then made to partial D antigens. The weak D characteristic is characterized in that it is a normal antigen, but the number of sites thereof per red blood cell is decreased more or less considerably; this characteristic is transmissible according to Mendelian laws. Partial D phenotypes have been discovered in Rh-D-positive individuals who have anti-D serum antibodies; these partial D antigens can therefore be characterized as having only part of the mosaic. Studies carried out with polyclonal and monoclonal antibodies have made it possible to define 7 categories of partial D antigens with at least 8 epitopes constituting the D antigen being described (LOMAS et al., 1989; TIPETT 1988).

The importance of anti-Rh D antibodies became apparent with the discovery of the mechanisms leading to hemolytic disease of the newborn (HDN). This corresponds to the various pathological conditions observed in some fetuses or in some newborn babies when there is a feto-maternal blood group incompatibility which is responsible for the formation of maternal anti-Rh D antibodies capable of crossing the placental barrier. In fact, fetal Rh-positive red blood cells passing into an Rh-negative mother can lead to the formation of anti-D antibodies.

After immunization of the Rh-negative mother, the IgG class anti-D antibodies are capable of crossing the placental barrier and of binding to the fetal Rh-positive red blood cells. This binding leads to the activation of immunocompetent cells via their surface Fc receptors, thus inducing hemolysis of the sensitized fetal red blood cells. Depending on the strength of the reaction, several degrees of seriousness of HDN can be observed.

An HDN diagnosis can be carried out before and after birth. Prenatal diagnosis is based on the development of the anti-D antibody level in the mother using several immunohematological techniques. Post-partum diagnosis may be carried out using an umbilical cord blood sample, analyzing the following parameters: determining the blood groups of the fetus and of the father; searching for anti-D antibodies; assaying the hemoglobin and the bilirubin.

Prophylactic treatment for HDN is currently systematically given to all women with an Rh-negative blood group who have given birth to an Rh-positive child, with injections of human anti-D immunoglobulin. The first real immunoprophylaxis trials began in 1964. For the prevention to be effective, the immunoglobulin must be injected before the immunization, i.e. within the 72 hours following the birth, and the antibody doses must be sufficient (10 μg of anti-D antibodies per 0.5 ml of Rh+ red blood cells).

Several anti-D monoclonal antibodies have been the subject of therapeutic assessment: BROSSARD/FNTS 1990 (not published); THOMSON/IBGRL 1990; KUMPEL/IBGRL 1994; BELKINA/Institute of hematology, Moscow, 1996; BIOTEST/LFB 1997 (not published). The clinical effectiveness of the antibodies in inducing clearance of Rh(D)-positive red blood cells was assessed in Rh(D)-negative volunteers.

A single IgG1 antibody showed an effectiveness equivalent to that of anti-D polyclonal immunoglobulins, but only in some patients (KUMPEL et al., 1995).

The invention proposes to provide monoclonal antibodies which reply to the abovementioned problems, i.e. antibodies selected using an assay of the ADCC type specific for the antibody and/or the antibodies having a glycan structure required for obtaining good effectiveness.

SUMMARY OF THE INVENTION

Thus, the present invention relates to a method for preparing a monoclonal antibody capable of activating effector cells expressing FcγRIII, characterized in that it comprises the following steps:

a. purifying monoclonal antibodies obtained from various clones originating from cell lines selected from hybridomas, in particular heterohybridomas, and animal or human cell lines transfected with a vector comprising the gene encoding said antibody;

b. adding each antibody obtained in step a) to a different reaction mixture comprising:
   the target cells for said antibodies,
   effector cells comprising cells expressing FcγRIII,
   polyvalent IgGs;

c. determining the percentage lysis of the target cells and selecting the monoclonal antibodies which activate the effector cells causing significant lysis of the target cells (FcγRIII-type ADCC activity).

The clones may originate from heterohybrid cell lines obtained by fusion of human B lymphocytes (originating from immunized individuals) with murine, human or heterohybrid myeloma cells, in particular the K6H6-B5 myeloma (ATCC No. CRL 1823); or else from animal or human cell lines transfected with a vector containing the gene encoding a human IgG immunoglobulin, said lines possibly being selected in particular from the CHO—K, CHO-Lec10, CHO Lec-1, CHO Pro-5, CHO dhfr-, Wil-2, Jurkat, Vero, Molt-4, COS-7, 293-HEK, YB2/0, BHK, K6H6, NSO, SP2/0-Ag 14 and P3X63Ag8.653 lines.

The polyvalent IgGs are used to inhibit the mechanism of lysis of the effector cells via FcγRI. In this method, the antibodies which exhibit an FcγRIII-type ADCC level greater than 60%, 70%, 80%, or preferably greater than 90%, are selected. The target cells can be red blood cells treated with papain. In this case, the following are deposited per well:
   100 μl of purified monoclonal antibodies at approximately 200 ng/ml,
   25 μl of papain-treated red blood cells, i.e. approximately $1 \times 10^6$ cells,
   25 μl of effector cells, i.e. approximately $2 \times 10^6$ cells,
   and 50 μl of polyvalent IgGs, in particular of TEGELINE™ (LFB, France), at a concentration of between 1 and 20 mg/ml.

It is thus possible to compare the amount of target cell lysis to two positive controls consisting of a chemical compound such as $NH_4Cl$ and a reference antibody active in vivo, and to a negative control consisting of an antibody inactive in vivo.

It is also possible to use polyclonal antibodies of commercial origin as positive controls and a monoclonal antibody incapable of inducing clearance in vivo as a negative control.

Advantageously, this method makes it possible to prepare anti-Rh(D) monoclonal antibodies as indicated above. Rhesus D red blood cells are then used as target cells.

The invention is therefore based on developing an assay for biological activity in vitro, in which the activities measured correlate with the biological activity in vivo of the monoclonal or polyclonal antibodies already evaluated from the clinical point of view with regard to their potentiality in inducing clearance of Rh(D)-positive red blood cells in Rh(D)-negative volunteers. This assay makes it possible to evaluate the antibody-dependent lytic activity=ADCC (antibody-dependent cellular cytotoxicity) induced essentially by the Fcγ type III receptors (CD16), the Fcγ type I receptors (CD64) being saturated by the addition of human IgG immunoglobulins (in the form of therapeutic polyvalent IgGs). The FcγRIII specificity of this ADCC assay was confirmed by inhibition in the presence of an anti-FcγRIII monoclonal antibody (see FIG. 6). Mononuclear cells from healthy individuals are used as effector cells in an effector/target (E/T) ratio close to physiological conditions in vivo. Under these conditions, the lytic activities of the polyclonal immunoglobulins and of the anti-D monoclonal antibodies ineffective in vivo (antibody DF5, Goossens et al., 1987, and the antibodies AD1+AD3, FR 92/07893 LFB/Biotest and FOG-1, GB 2189506) are, respectively, strong and weak.

The selection of the antibodies described in the present invention was therefore carried out by evaluating their biological activity in this ADCC-type assay (see example 1).

In another aspect, the invention relates to the antibodies which can be obtained using the method described above, said antibodies exhibiting FcγRIII-type ADCC levels greater than 60%, 70%, 80%, or preferably greater than 90%, relative to the reference polyclonal. The monoclonal antibodies of the invention, directed against a given antigen, activate effector cells expressing FcγRIII, causing lysis greater than 60%, 70%, 80%, preferably greater than 90%, of the lysis caused by polyclonal antibodies directed against said antigen. Advantageously, said monoclonal antibodies are directed against rhesus D.

They may preferably be produced by clones derived from the Vero (ATCC No. CCL 81), YB2/0 (ATTC No. CRL 1662) or CHO Lec-1 (ATCC No. CRL 1735) lines and may belong to the IgG1 or IgG3 class.

The invention also relates to antibodies which have a particular glycan structure conferring FcγRIII-dependent effector activity.

Such antibodies can be obtained using a method explained above and have, on their Fcγ glycosylation site (Asn 297), glycan structures of the bi-antennary type, with short chains and a low degree of sialylation. Preferably, their glycan structure exhibits nonintercalated terminal mannoses and/or terminal GlcNAcs.

Such antibodies are more particularly selected from the forms shown in FIG. 10.

Thus, the invention is directed toward a monoclonal antibody characterized in that it has, on its Fcγ glycosylation site (Asn 297), glycan structures of the bi-antennary type, with short chains, a low degree of sialylation, and nonintercalated mannoses and GlcNAcs with a terminal point of attachment. Said antibodies, directed against a given antigen, activate effector cells expressing FcγRIII, causing lysis greater than 60%, 70%, 80%, preferably greater than 90%, of the lysis caused by polyclonal antibodies directed against said antigen.

More particularly, the invention relates to antibodies and compositions comprising said antibodies as defined above, in which the sialic acid content is less than 25%, 20%, 15% or 10%, preferably 5%, 4%, 3% or 2%.

Similarly, the invention relates to antibodies and compositions comprising said antibodies as defined above, in which the fucose content is less than 65%, 60%, 50%, 40% or 30%. Preferably, the fucose content is between 20% and 45%, or else between 25% and 40%.

A particularly effective composition according to the invention comprises, for example, a content greater than 60%, preferably greater than 80%, for the G0+G1+G0F+G1F forms, it being understood that the G0F+G1F forms are less than 50%, preferably less than 30%.

TABLE 1

Quantification (%) of the oligosaccharide structures of the various anti-RhD antibodies

| | Antibodies active by FcRγIII ADCC | | | | | Antibodies inactive by FcRγIII ADCC | | |
|---|---|---|---|---|---|---|---|---|
| | R297 | R270 | | F60 | | D31 | | |
| Structure | HPCE-LIF | HPCE-LIF | HPLCs | HPCE-LIF | HPLCs | HPCE-LIF | HPCE-LIF | F5 HPLCs |
| Fucosylated | 34.3 | 45.9 | 37.2 | 47.7 | 46.6 | 82.0 | 88 | 100 |
| Sialylated | 1.0 | 2.2 | 4.1 | 9.9 | 19.6 | 47.9 | 52.0 | 17 |
| G2S2FB | | | | | | | | 2.8 |
| G2S2F | 0.0 | 0.0 | n.d. | 4.2 | 0.0 | 11.3 | 11.9 | 4.1 |
| G2S1FB | | | | | | | | 6.1 |
| G2S1F | 1.0 | 1.0 | n.d. | 2.7 | 2.5 | 21.4 | 30.5 | 28 |
| G2S1 | 0.0 | 1.2 | n.d. | 3.0 | 0.0 | 0 | 0 | |
| G1S1FB | | | | | | | | 6.2 |
| G1S1F | | | | | | | | 1.7 |
| G2F | 3.9 | 5.0 | 3.0 | 10.3 | 11.6 | 16.9 | 22.1 | 4.2 |
| G2 | 12.1 | 6.1 | 3.3 | 7.0 | 13.3 | 2.0 | 0.0 | 0.0 |
| G1FB | | | | | | | | 25.7 |
| G1F | 17.4 | 16.9 | 15 | 24.8 | 22.1 | 16.1 | 21.5 | 12.4 |
| G1 | 26.1 | 11.3 | 21.0 | 22.2 | 22.8 | 0.0 | 0.0 | 0.0 |
| G0F | 12.1 | 23.1 | 19.4 | 5.6 | 10.5 | 1.7 | 3.0 | 0.0 |
| G0 | 29.1 | 32.7 | 38.5 | 15.8 | 17.7 | 13.6 | 13.9 | 0.5 |

An alternative for specifically targeting FcγRIII consists in preparing antibodies of the "high mannose" type.

In another aspect, the invention relates to a cell producing an antibody mentioned above. It may be a hybridoma, in particular a heterohybridoma obtained with the fusion partner K6H6-B5 (ATCC No. CRL 1823); or an animal or human cell transfected with a vector comprising the gene encoding said antibody, in particular a cell derived from the Vero (ATCC No. CCL 81), YB2/0 (ATCC No. CRL 1662) or CHO Lec-1 (ATCC No. CRL 1735) lines. These cells correspond to the cell lines selected using the method according to the invention, said cells producing antibodies which have the characteristics mentioned above.

A preferred antibody according to the invention shows considerable biological activity (greater than or equal to that of the anti-Rh(D) reference polyclonal antibody) in the ADCC assay using FcγRIII-positive effector cells.

Its ability to activate FcγRIII receptors (after binding) is confirmed on in vitro models which demonstrate modification of intracellular calcium flux, phosphorylation of activation signal transduction molecules, or release of chemical mediators.

These properties are associated with a particular structure of the oligosaccharides of the N-glycosylation site of the Fc component of the antibody: presence of short chains, low degree of galactosylation, little sialylation, may have non-intercalated terminal mannoses and/or terminal GlcNAcs, for example.

This antibody has therapeutic applications: prevention of HDN, treatment of ITP in Rh(D)-positive individuals, and any other application to which the use of anti-D polyclonal immunoglobulins relates.

A preferred antibody according to the invention may also have a specificity other than anti-Rh(D) (anti-cancer cell for example). It may have the properties described above (functional activity dependent on a mechanism of binding to/activation of FcγRIII receptors, particular structure of oligosaccharides) and may be used in immunotherapy for cancers or for any other pathological condition for which a curative or preventive treatment may be carried out using a monoclonal antibody the mechanism of action of which corresponds to an activity which is functional via the FcγRIII receptor.

Another aspect relates to a pharmaceutical composition comprising an antibody according to the invention and to the use of said antibody for producing a medicinal product.

Preferably, the invention relates to the use of an anti-Rh(D) antibody described above, for producing a medicinal product intended for the prevention of Rhesus alloimmunization of Rh-negative individuals. The method of action of the anti-D immunoglobulins in vivo is specific binding of the antibodies to the D antigen of the Rh(D)-positive red blood cells, followed by elimination of these red blood cells from the circulation essentially in the spleen. This clearance is associated with a dynamic mechanism of suppression of primary immune response in the individual, and therefore prevents the immunization.

Thus, an antibody of the invention may be used prophylactically for preventing alloimmunization of Rhesus-negative women immediately after the birth of a Rhesus-positive child, and for preventing, at the time of subsequent pregnancies, hemolytic disease of the newborn (HDN); at the time of abortions or of extra-uterine pregnancies in a situation of Rhesus D incompatibility or else at the time of transplacental hemorrhages resulting from amniocentesis, from chorionic biopsies or from traumatic obstetric manipulations in a situation of Rhesus D incompatibility.

In addition, an antibody of the invention may be used in the case of Rh-incompatible transfusions with blood or labile blood derivatives.

The invention also relates to the use of an antibody of the invention for producing a medicinal product intended for therapeutic use in Idiopathic Thrombocytopenic Purpura (ITP).

The antibodies of the invention are also of use for producing a medicinal product intended for the treatment of cancers by immunotherapy, or for the treatment of infections caused by viral or bacterial pathogenic agents.

An additional aspect of the invention relates to the use of said antibodies in particular for diagnosis. The invention is therefore directed toward a kit comprising an antibody described above.

For the remainder of the description, reference will be made to the legends of the figures presented below.

The ADCC assay is established according to the procedure described in §3.3 in the presence of the commercial anti-CD16 3G8 (TEBU), the action of which is to block the FcRIII receptors present on the effector cells. The final concentration of 3G8 is 5 μg/well (25 μg/ml). A control is carried out in parallel in the absence of 3G8.

The three antibodies tested are Poly-D WinRho, the antibody F60 (Pf 155 99/47) obtained according to the method described in example I, and R297 (Pf 210 01/76) obtained according to the method described in example II.

Results: an inhibition is observed in the presence of 3G8, which demonstrates that the ADCC induced by the three antibodies tested is mainly FcRIII-dependent. A slightly stronger inhibition is observed in the presence of Poly-D WinRho (83% compared to 68% and 61% inhibition for F60 and R297, respectively). This difference may be due to the presence, in the Poly-D, of non-anti-D human IgGs which will inhibit type I receptors (FCR1 or CD64) and therefore act synergistically with the anti-CD 16.

Figure 7:
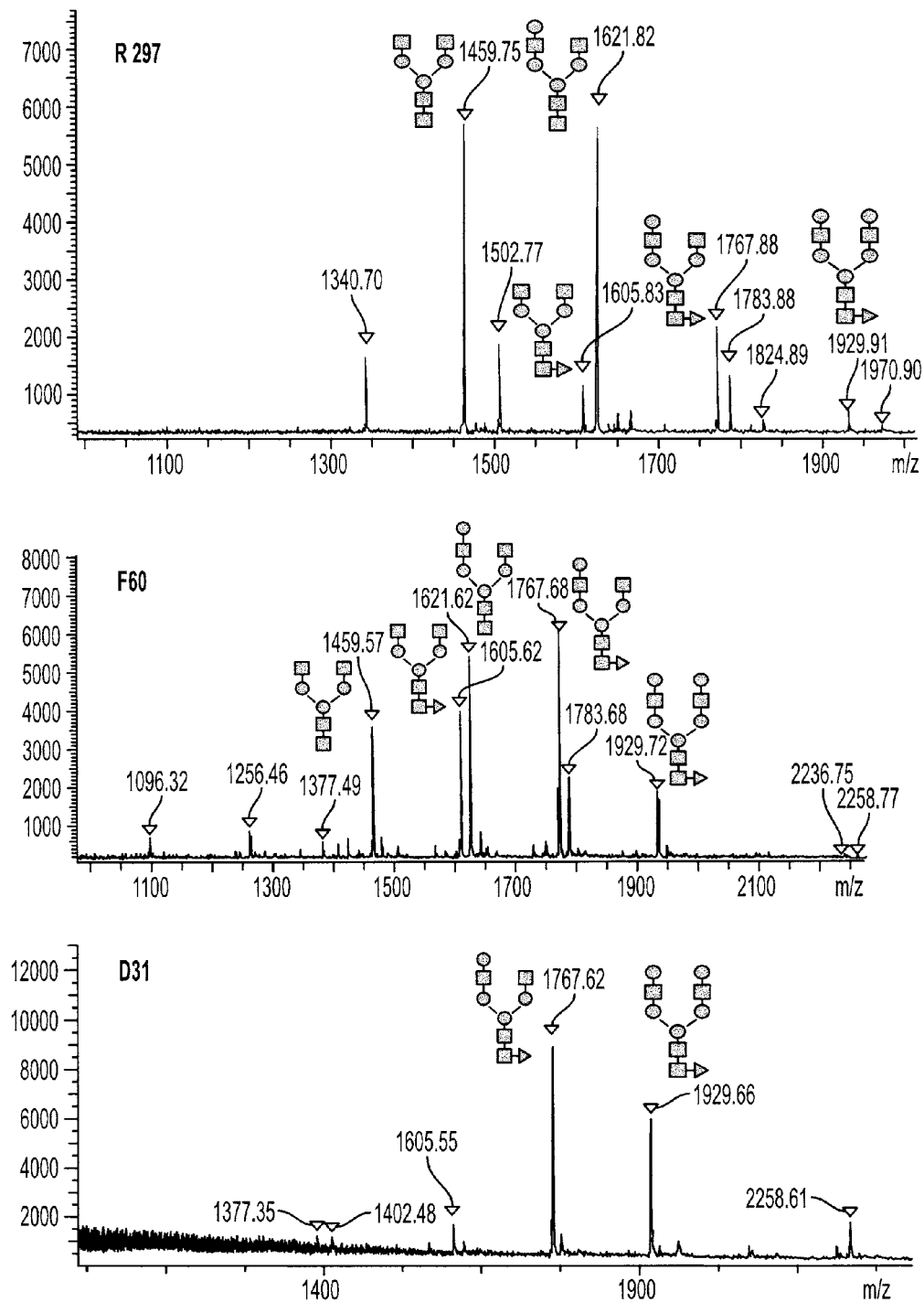

FIG. 7: Characterization of the anti-D glycans by mass spectrometry (MS).

Figure 8:
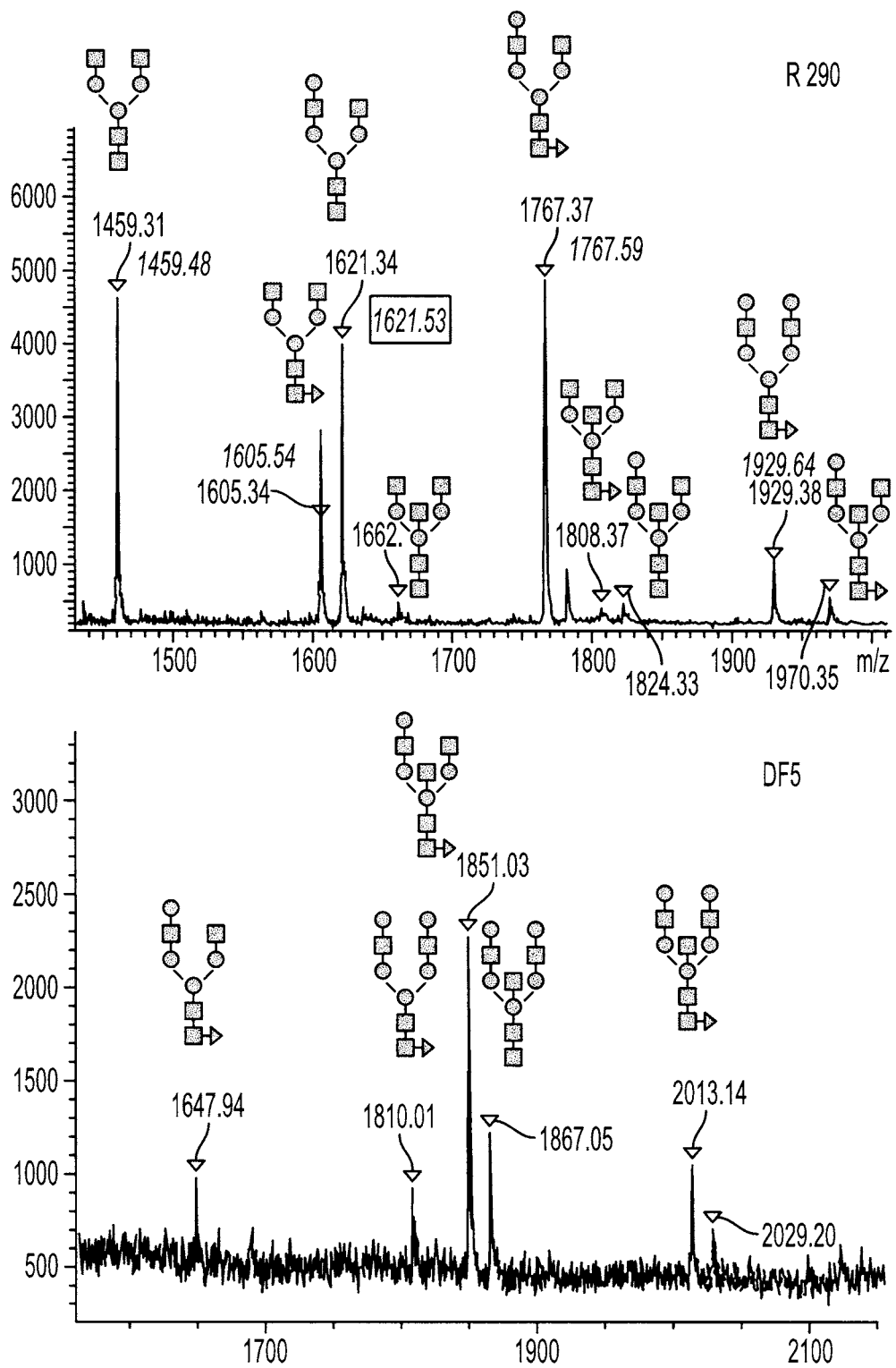

FIG. 8: Comparison of the MS spectra for 8290 and DF5.

Figure 9:
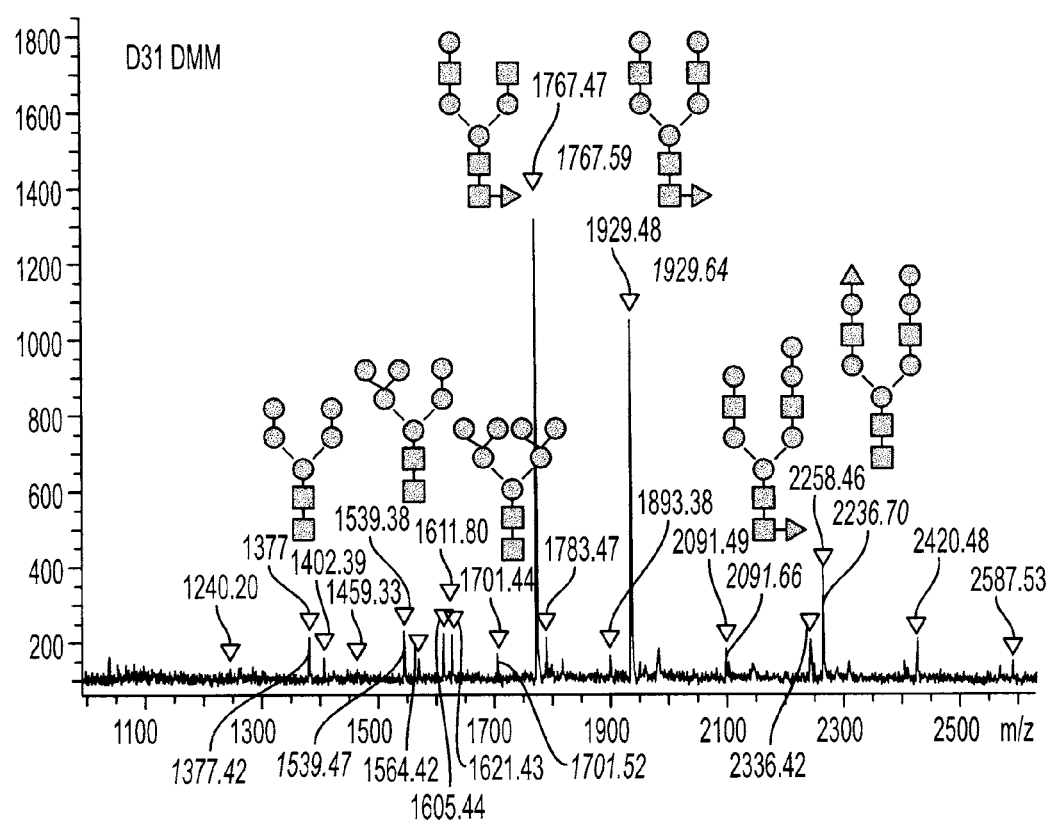

FIG. 9: Study of the glycosylation of the anti-D D31DMM by MS.

Figure 10:
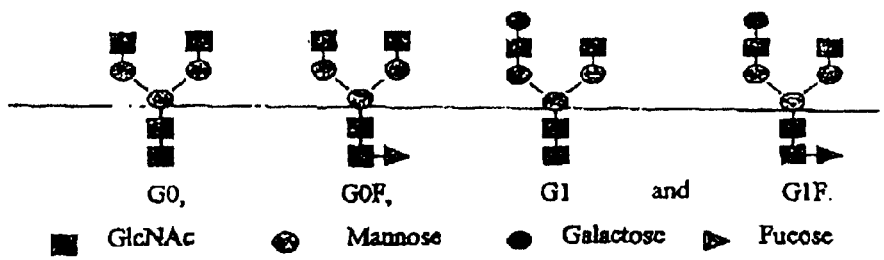

FIG. 10: Preferred embodiments of antibodies having a particular glycan structure conferring FcγRIII-dependent effector activity.

Figure 11:
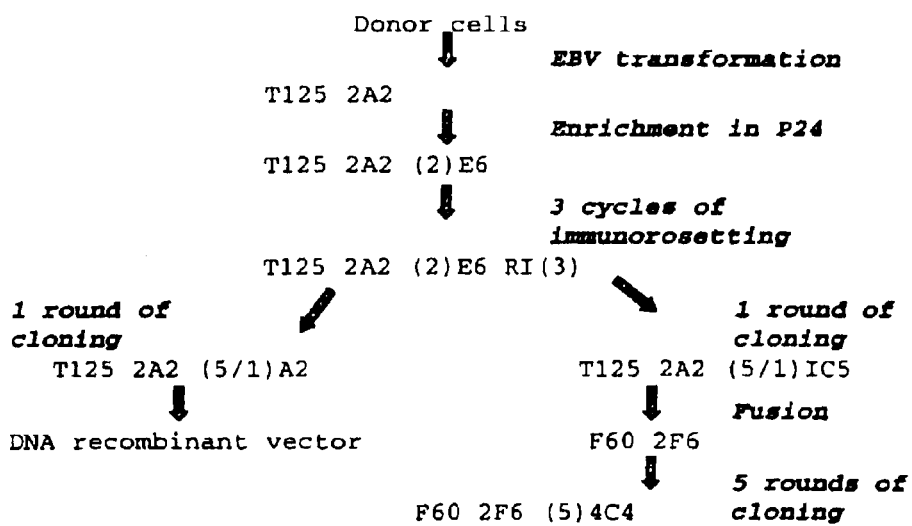

FIG. 11: A preferred embodiment for producing an IgG1 possessing a Kappa light chain.

Figure 12:
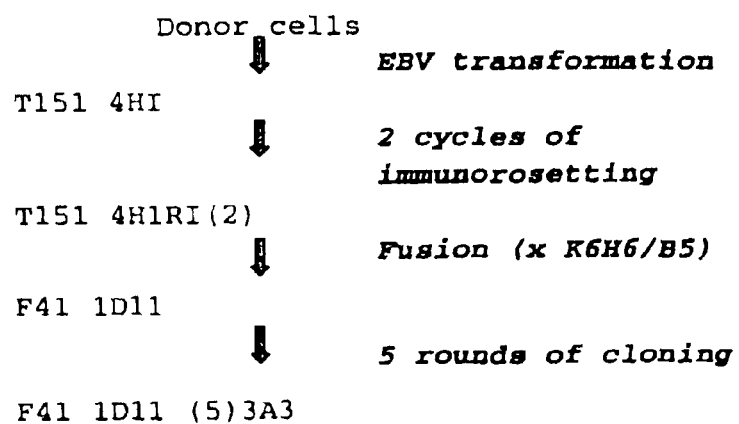

FIG. 12: A preferred embodiment for producing an IgG3 possessing a Kappa light chain.

DETAILED DESCRIPTION OF THE PREFERRED EMBODIMENTS

Example 1

Establishing a Heterohybrid Cell Line Producing an Anti-Rh(D) Antibody

1—Production of Lymphoblastoid and Heterohybrid Clones:
1.1—Lymphocyte Source:

The B lymphocyte donor is selected from anti-Rh(D) donors undergoing plasmapheresis, based on the activity of his or her anti-Rh(D) serum antibodies in the ADCC activity assay described in §33. After a whole blood donation, in 1998, the "buffy coat" fraction (leukocyte concentrate) was recovered.

1.2—Immortalization of the B Lymphocytes from the Donor

The peripheral blood mononuclear cells are separated from the other elements by centrifugation on Ficoll Plus (Pharmacia). They are then diluted to $10^6$ cell/ml in IMDM containing 20% (v/v) of fetal calf serum (FCS), to which 20% of culture supernatant of the B95-8 line (ATCC-CRL1612), 0.1 μg/ml of cyclosporin A (Sandoz), 50 μg/ml of gentamycin sulfate (Life Technologies) are added, and distributed into round-bottomed 96-well plates or 24-well plates (P24 Greiner). They are then placed in an incubator at 37° C., 7% $CO_2$. After 3 weeks, the presence of anti-Rh(D) antibodies is sought by ADCC.

Each one of the 16 microwells of a positive P24 plate well is transferred into a new P24 well. This enrichment is repeated after 10 to 15 days of culturing and each microwell is amplified in a P96 and then in a P24.

The positive P96 wells are taken up and amplified in a flat-bottomed P24 (Nunc). After a few days of culturing, the presence of anti-Rh(D) antibodies is sought by ADCC.

1.3—Enrichment by Immunorosetting (IR):

The cells derived from one or more P24 wells are enriched in specific cells by the formation and separation of rosettes with papain-treated Rh(D)-positive red blood cells: one volume of red blood cells washed in 0.9% NaCl is incubated for 10 minutes at 37° C. with 1 volume of papain (Merck) solution at 1/1 000th (m/v), and then washed 3 times in 0.9% NaCl. The cells were then washed once in Hanks solution, suspended in FCS and mixed with the papain-treated red blood cells in a ratio of 1 cell to 33 red blood cells. The mixture is placed in a cone-bottomed centrifuged tube, centrifuged for 5 minutes at 80 g and incubated for one hour in melting ice. The mixture is then carefully agitated and Ficoll is deposited at the bottom of the tube for separation at 900 g for 20 minutes. The pellet containing the rosettes is hemolyzed in a solution of $NH_4Cl$ for 5 minutes and the cells are placed in culture again in a P24 containing irradiated human mononuclear cells. After approximately 1 week, the supernatants are evaluated in CELA (paragraph 3.2) and ADCC assays for the presence of anti-Rh(D) antibodies having good activity. A further cycle of enrichment is carried out if the percentage of cells forming rosettes significantly increases compared to the preceding cycle.

1.4—Cloning of the Lymphoblastoid Cells:

The IR-enriched cells are distributed at 5 and 0.5 cells per well in round-bottomed 96-well plates containing irradiated human mononuclear cells.

After approximately 4 weeks of culturing, the supernatants from the wells containing cell aggregates are evaluated by ADCC assay.

1.5—Heterofusion:

The wells from cloning the EBV-transformed cells exhibiting an advantageous ADCC activity are amplified in culture and then fused with the heteromyeloma K6H6-B5 (ATCC CRL-1823) according to the standard PEG technique. After fusion, the cells are distributed, in a proportion of $2 \times 10^4$ cells/well, into flat-bottomed P96s containing murine intraperitoneal macrophages and in a selective medium containing aminopterin and ouabain (Sigma).

After 3 to 4 weeks of culturing, the supernatants of the wells containing cell aggregates are evaluated by ADCC assay.

1.6—Cloning of the Heterohybridomas:

Cloning by limiting dilution is carried out at 4, 2 and 1 cell/well in flat-bottomed P96s. After 2 weeks, the microscopic appearance of the wells is examined in order to identify the single clones, and the medium is then renewed. After approximately 2 weeks, the supernatants of the wells containing cell aggregates are evaluated by ADCC assay.

2—History of the Clones Selected:

2.1—Clone producing an IgG1

EBV transformation of the cells of donor d13 made it possible to select a well, designated T125 2A2, on which the following were successively carried out: 2 enrichments, 3 cycles of IR, and cloning at 5 cells/well to give 2 clones:
1) T125 2A2 (5/1)A2 from which the DNA was extracted in order to prepare the recombinant vector;
2) T125 (5/1)A2 which was fused with K6H6-B5 to give F60 2F6 and then, after 5 rounds of cloning, F60 2F6 (5) 4C4, a clone selected for constituting a cell stock prior to preparing libraries.

It is an IgG1 possessing a Kappa light chain. The method is shown in FIG. 11.

2.2—Clone Producing an IgG3

A line producing an IgG3 was prepared according to the same method as that used to prepare the antibody of IgG1 isotype. The cells of origin originate from a donation of whole blood, from a designated donor, from which the "buffy coat" fraction (leukocyte concentrate) was recovered.

It is an IgG3 possessing a Kappa light chain. The method is shown in FIG. 12.

3—Methods for Evaluating the Anti-Rh(D) Antibodies:

After purification by affinity chromatography on protein A sepharose (Pharmacia) and dialysis in 25 mM Tris buffer, 150 mM NaCl, pH 7.4, the concentration of the antibody T125 is determined by the ELISA technique. The biological activity in vitro is then measured by the ADCC technique.

3.1—Determination of the IgG Level and of the Isotypes by the ELISA Technique:

Total IgGs

Coating: anti-IgG (Calbiochem) at 2 µg/ml in 0.05M carbonate buffer, pH 9.5, overnight at 4° C. Saturation: dilution buffer (PBS+1% BSA+0.05% Tween 20, pH 7.2), 1 h at ambient temperature. Washing (to be renewed at each step): $H_2O$+150 mM NaCl+0.05% Tween 20. Dilution of the samples, in dilution buffer to approximately 100 ng/ml and of the control range made up of LFB polyvalent human IgGs prediluted to 100 ng/ml. Incubation for 2 h at ambient temperature. Conjugate: anti-IgG (Diagnostic Pasteur) diluted to 1/5 000, 2 hours at ambient temperature. Substrate: OPD at 0.5 mg/ml (Sigma) in phosphate-citrate buffer containing sodium perborate (Sigma), 10 minutes in the dark. Reaction stopped with 1N HCl, and read at 492 nm.

Assaying of Kappa Chain

Coating: anti-Kappa (Caltag Lab) at 5 µg/ml in 0.05M carbonate buffer, pH 9.5, overnight at 4° C. Saturation: dilution buffer (PBS+1% BSA+0.05% Tween 20, pH 7.2), 1 h at ambient temperature. The washing (to be renewed at each step): $H_2O$+150 mM NaCl+0.05% Tween 20. Dilution of the samples, in dilution buffer, to approximately 100 ng/ml and of the control range made up of the LFB monoclonal antibody AD3T1 (Kappa/gamma 3) prediluted to 100 ng/ml. Incubation for 2 h at ambient temperature. Conjugate: biotinylated anti-Kappa (Pierce) diluted to 1/1 000 in the presence of streptavidin-peroxidase (Pierce) diluted to 1/1 500, 2 hours at ambient temperature. Substrate: OPD at 0.5 mg/ml (sigma) in phosphate-citrate buffer containing sodium perborate (Sigma), 10 minutes in the dark. The reaction is stopped with 1N HCl, and read at 492 nm.

3.2—Specific Assaying of Anti-D by the CELA (Cellular Enzyme Linked Assay) Technique:

This method is used for specifically assaying the anti-D antibodies in particular when this involves a culture supernatant at culturing stages at which other non-anti-D immunoglobulins are present in the solution (early stages after EBV transformation).

Principle: The anti-D antibody is incubated with Rhesus-positive red blood cells and then revealed with an alkaline phosphatase-labeled anti-human Ig.

100 µl of Rh+ red blood cells at 10% diluted in Liss-1% BSA dilution buffer. Dilution of the samples, in dilution buffer, to approximately 500 ng/ml and of the control range made up of a purified monoclonal human anti-D IgG (DF5, LFB) prediluted to 500 ng/ml. Incubation for 45 min at ambient temperature. Washing (to be renewed at each step): $H_2O$+150 mM NaCl. Conjugate: anti-IgG alkaline phosphatase (Jackson) diluted to 1/4 000 in PBS+1% BSA, 1 h 30 at ambient temperature. Substrate: PNPP at 1 mg/ml (sigma) in 1M diethanolamine, 0.5 mM $MgCl_2$, pH 9.8. The reaction is stopped with 1N NaOH, and read at 405 nm.

3.3—ADCC Technique

The ADCC (antibody-dependent cellular cytotoxicity) technique makes it possible to evaluate the ability of the (anti-D) antibodies to induce lysis of Rh-positive red blood cells, in the presence of effector cells (mononuclear cells or lymphocytes).

Briefly, the red blood cells of an Rh-positive cell concentrate are treated with papain (1 mg/ml, 10 min at 37° C.) and then washed in 0.9% NaCl. The effector cells are isolated from a pool of at least 3 buffy-coats, by centrifugation on Ficoll (Pharmacia), followed by a step of adhesion in the presence of 25% FCS, so as to obtain a lymphocyte/monocyte ratio of the order of 9. The following are deposited, per well, into a microtitration plate (96 well): 100 µl of purified anti-D antibody at 200 ng/ml, 25 µl of Rh+ papain-treated red blood cells (i.e. $1\times10^6$), 25 µl of effector cells (i.e. $2\times10^6$) and 50 µl of polyvalent IgG (Tegeline, LFB, for example) at the usual concentrations of 10 and 2 mg/ml. The dilutions are made in IMDM containing 0.25% FCS. After overnight incubation at 37° C., the plates are centrifuged, and the hemoglobin released into the supernatant is then measured in the presence of a substrate specific for peroxidase activity (2,7-diaminofluorene, DAF). The results are expressed as percentage lysis, 100% corresponding to total red blood cell lysis in $NH_4Cl$ (100% control), and 0% to the reaction mixture without antibody (0% control).

The specific lysis is calculated as a percentage according to the following formula:

$$\frac{(OD \text{ sample} - OD \text{ 0\% control}) \times 100}{OD \text{ 100\% control} - OD \text{ 0\% control}} = \% \, ADCC$$

Figure 1:
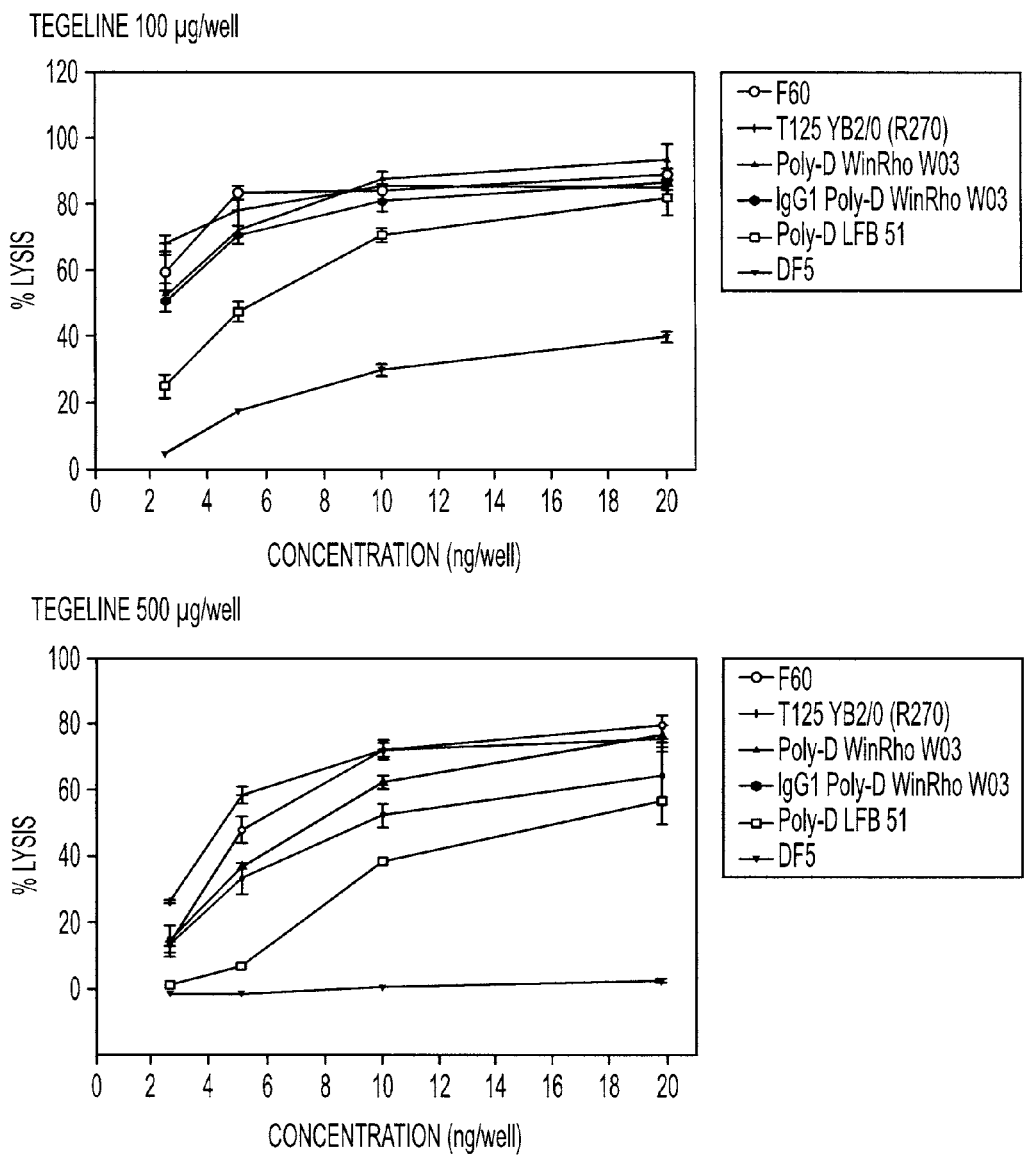
FIG. 1: ADCC evaluation of F60 and T125 YB2/0 (R270). This figure represents the percentage lysis obtained as a function of the antibody concentration in the presence of 100 and 500 μg/well of TEGELINE™ (LFB, France). A high percentage lysis is obtained for the antibodies according to the invention F60 and T125.

The results given in FIG. 1 show the activity of the antibody produced by the heterohybrid F60 compared to those of the reference antibodies:

the anti-Rh(D) polyclonal antibodies POLY-D LFB 51 and WinRhO W03 (Cangene)=positive controls the monoclonal antibody DF5 (inactive in vivo on clearance of Rh(D)-positive red blood cells (BROSSARD/FNTS, 1990, not published))=negative control the IgG1s purified (separated from the IgG3s) from the polyclonal WinRhO W03.

Two concentrations of human IgGs (Tegeline LFB) are used to show that inhibition of activity of the negative control is linked to the binding of competing IgGs to the Fcγ type I receptors.

3.4—FcγRIII(CD16)-Binding Technique:

This assay makes it possible to assess the binding of the anti-Rh(D) antibodies of IgG1 isotype to FcγRIII, and in particular to differentiate IgG3 antibodies. Given the low affinity of this receptor for monomeric IgGs, prior binding of the antibodies to the D antigen is necessary.

Principle: The antibody to be tested (anti-D) is added to membranes of Rh+ red blood cells coated with a microtitration plate, followed by transfected Jurkat cells expressing the FcγRIII receptor at their surface. After centrifugation, the "Rh+ membrane/anti-D/CD16 Jurkat" interaction is visualized by a homogeneous plating of the CD16 Jurkats in the well. In the absence of interaction, the cells are, on the contrary, grouped at the center of the well. The intensity of the reaction is expressed as numbers of +.

Method: 1) Incubation for 1 h at 37° C. of the anti-D antibody (50 μl at 1 μg/ml in IMDM) on a Capture R plate (Immunochim), and then washes in water+0.9% NaCl. Addition of CD16 Jurkat ($2\times10^6$ cells/ml) in IMDM+10% FCS. Incubation for 20 min at 37° C. and then centrifugation and evaluation of cell adhesion (against a control range).

2) Revelation of the anti-D bound to the Capture R plates by an ELISA-type technique using anti-human IgG-peroxidase at 1/5 000 (Sanofi Diagnostics Pasteur) after having lysed the CD16 Jurkat cells with 0.2M Tris-HCl, 6M urea, pH 5.3-5.5. OPD revelation and then reading of optical density (O.D.) at 492 nm.

Expression of results: an arbitrary value of 0 to 3 is allotted as a function of the binding and of the plating of the CD16 Jurkat cells. These values are allotted at each OD interval defined (increments of 0.1). The following are plotted:

either a curve: adhesion of the Jurkat cells (Y) as a function of the amount of anti-D bound to the red blood cell membranes (X).

or a histogram of the "binding indices" corresponding, for each antibody, to the sum of each Jurkat cell binding value (0 to 3) allotted per OD interval (over a portion common to all the antibodies tested).

Figure 2:
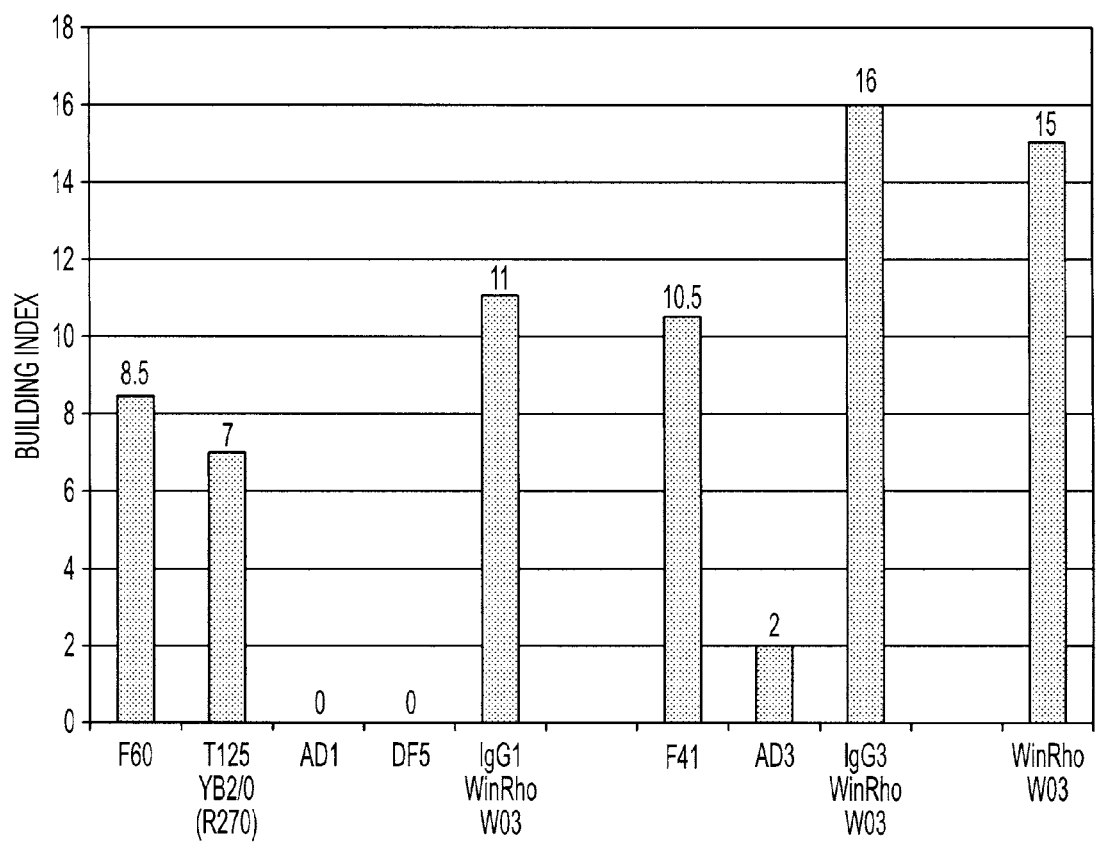
FIG. 2: Anti-D binding to the receptor (FcγRIII). A high binding index is obtained for the antibodies according to the invention F60 and T125.

An example of a histogram is given in FIG. 2.

The anti-Rh(D) antibodies of IgG1 isotype (F60 and T125 YB2/0) show a binding index close to that of the polyclonal IgG1s (WinRho), whereas the negative control antibodies DF5 and AD1 do not bind. Similarly, the antibody of IgG3 isotype (F41) exhibits a good binding index, slightly less than that of the IgG3s purified from the polyclonal Winrho and greater than that of the antibody AD3 (other IgG3 tested and ineffective in clinical trial, in a mixture with AD1 (Biotest/LFB, 1997, not published).

Example 2

Production of a Recombinant Anti-D Antibody (Ab)

1—Isolation and Amplification of the cDNAs Encoding the Heavy and Light Chains of the Ab
1.1—RNA Extraction and cDNA Synthesis The total RNAs were extracted from an anti-D Ab-producing clone (IgG G1/Kappa) obtained by EBV transformation: T125 A2 (5/1) A2 (see paragraph 2, example 1).

The corresponding cDNAs were synthesized by reverse transcription of the total RNAs using oligo dT primers.
1.2—Amplification of the Variable Region of the Heavy Chain of T125-A2: VH/T125-A2 Sequence The VH/T125-A2 sequence is obtained by amplification of the T125-A2 cDNAs using the following primers:
primer A2VH5, located 5' of the leader region of the VH gene of T125-A2, introduces a consensus leader sequence (in bold) deduced from leader sequences already published and associated with VH genes belonging to the same VH3-30 family as the VH gene of T125-A2; this sequence also comprises an Eco RI restriction site (in italics) and a Kozak sequence (underlined):

```
A2VH5 (SEQ ID No. 1):
5'-CTCTCCGAATTCGCCGCCACCATGGAGTTTGGGCTGAGCTGGGT-3'
``` antisense primer GSP2ANP, located 5' of the constant region (CH) of T125-A2:

```
GSP2ANP (SEQ ID No. 2):
5'-GGAAGTAGTCCTTGACCAGGCAG-3'.
```

1.3—Amplification of the Constant Region of T125-A2: CH/T125-A2 Sequence

The CH/T125-A2 sequence is obtained by amplification of the T125-A2 cDNAs using the following primers:
primer G1, located 5' of the CH region of T125-A2:

```
G1 (SEQ ID No. 3):
5'-CCCTCCACCAAGGGCCCATCGGTC-3'
```

The first G base of the CH sequence is here replaced with a C (underlined) in order to recreate, after cloning, an Eco RI site (see paragraph 2.1.1).
antisense primer H3'Xba, located 3' of the CH of T125-A2, introduces an Xba I site (underlined) 3' of the amplified sequence:

```
H3'Xba (SEQ ID No. 4):
5'-GAGAGGTCTAGACTATTTACCCGGAGACAGGGAGAG-3'
```

1.4—Amplification of the Kappa Light Chain: K/T125-A2 Sequence

The entire Kappa chain of T125-A2 (K/T125-A2 sequence) is amplified from the T125-A2 cDNAs using the following primers:
primer A2VK3, located 5' of the leader region of the VK gene of T125-A2, introduces a consensus sequence (in bold) deduced from the sequence of several leader regions of VK VH genes belonging to the same VK1 subgroup as the VK gene of T125-A2; this sequence also comprises an Eco RI restriction site (in italics) and a Kozak sequence (underlined):

```
A2VK3 (SEQ ID No. 5):
5'-CCTACCGAATTCGCCGCCACCATGGACATGAGGGTCCCCGCTCA-3'
``` antisense primer KSE1, located 3' of Kappa, introduces an Eco RI site (underlined):

```
KSE1 (SEQ ID No. 6):
5'-GGTGGTGAATTCCTAACACTCTCCCCTGTTGAAGCTCTT-3'.
```

FIG. 1 gives a diagrammatic illustration of the strategies for amplifying the heavy and light chains of T125-A2.
2—Construction of Expression Vectors
2.1—Vector for Expressing the Heavy Chain of T125-A2: T125-H26

The construction of T125-H26 is summarized in FIG. 2. It is carried out in two stages: first of all, construction of the intermediate vector V51-CH/T125-A2 by insertion of the constant region of T125-A2 into the expression vector V51 derived from pCI-neo (FIG. 3) and then cloning of the variable region into V51-CH/T125-A2.

2.1.1—Cloning of the Constant Region of T125-A2

Figure 3:
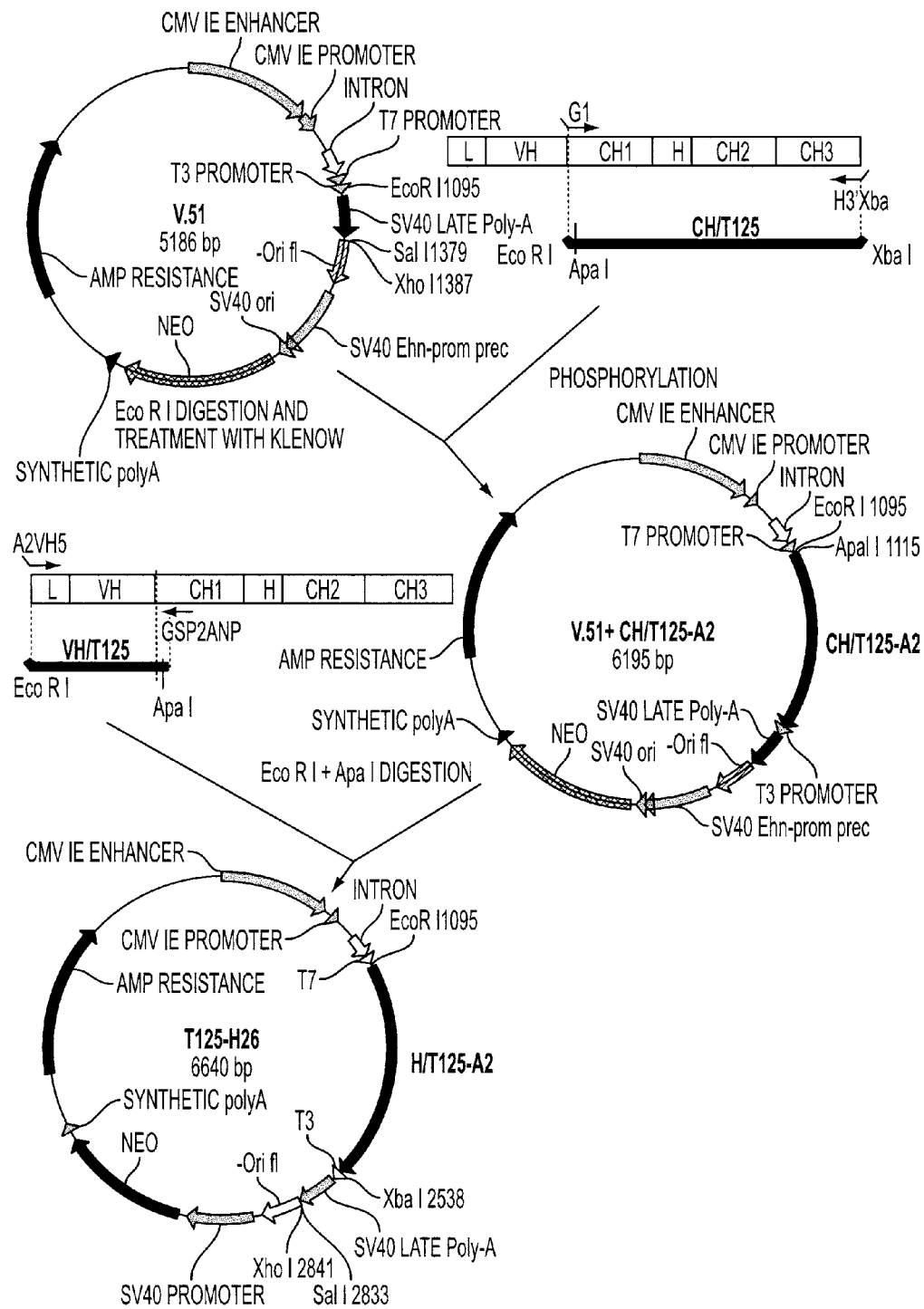
FIG. 3: Construction of the expression vector T125-H26 for expressing the H chain of T125.

The amplified CH/T125-A2 sequence is inserted, after phosphorylation, at the Eco RI site of the vector V51 (FIG. 3). The ligation is performed after prior treatment of the Eco RI sticky ends of V51 with the Klenow polymerase in order to make them "blunt-ended."

The primer G1 used for amplifying CH/T125-A2 makes it possible to recreate, after its insertion into V51, an Eco RI site 5' of CH/T125-A2.

2.1.2—Cloning of the Variable Region of T125-A2

The VH/T125-A2 sequence obtained by amplification is digested with Eco RI and Apa I and then inserted at the Eco RI and Apa I sites of the vector V51-G1/T125-A2.

2.2—T125-A2 Light Chain Vector: T125-K47

Figure 4:
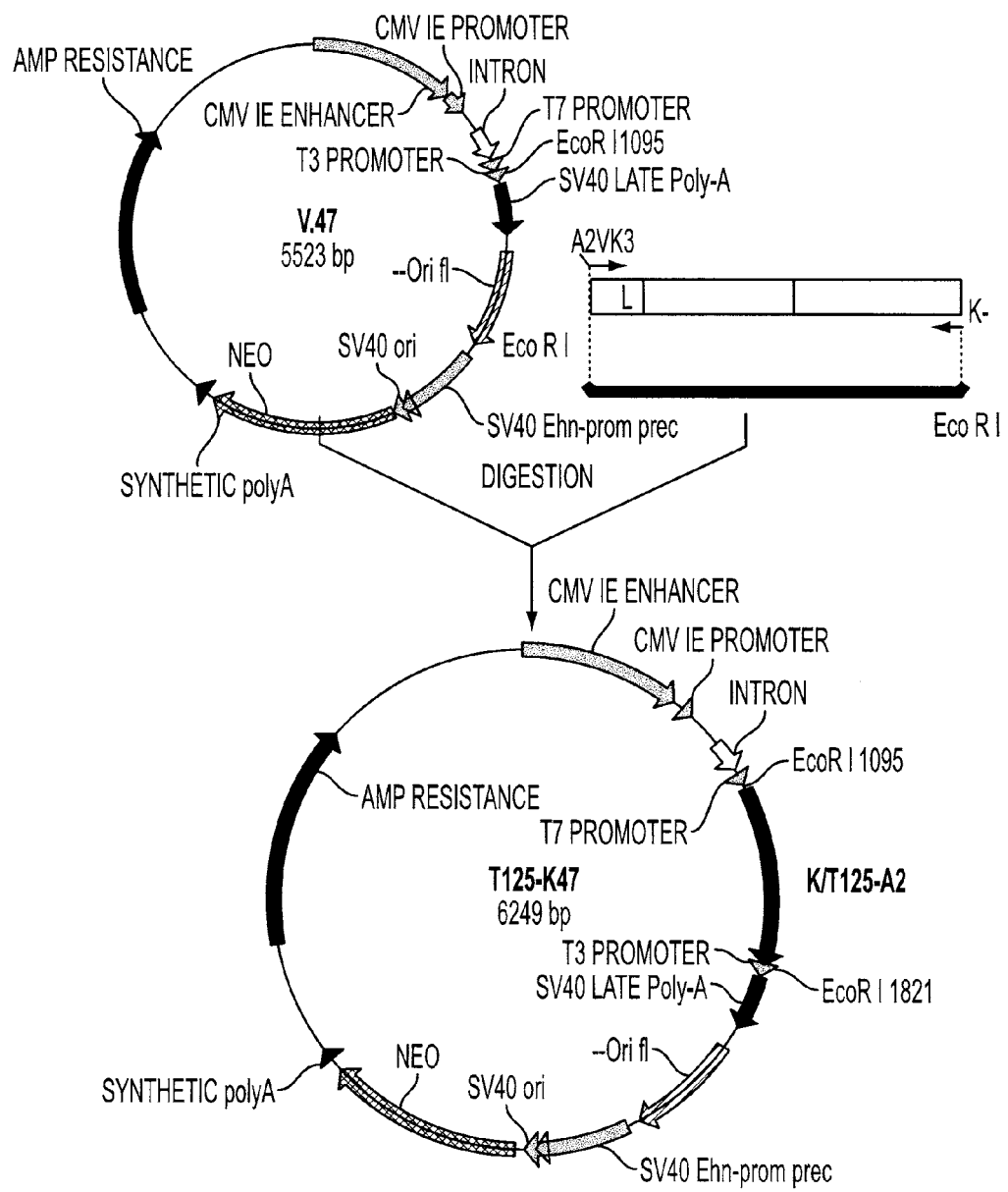
FIG. 4: Construction of the expression vector T125-K47 for expressing the L chain of T125
Figure 5:
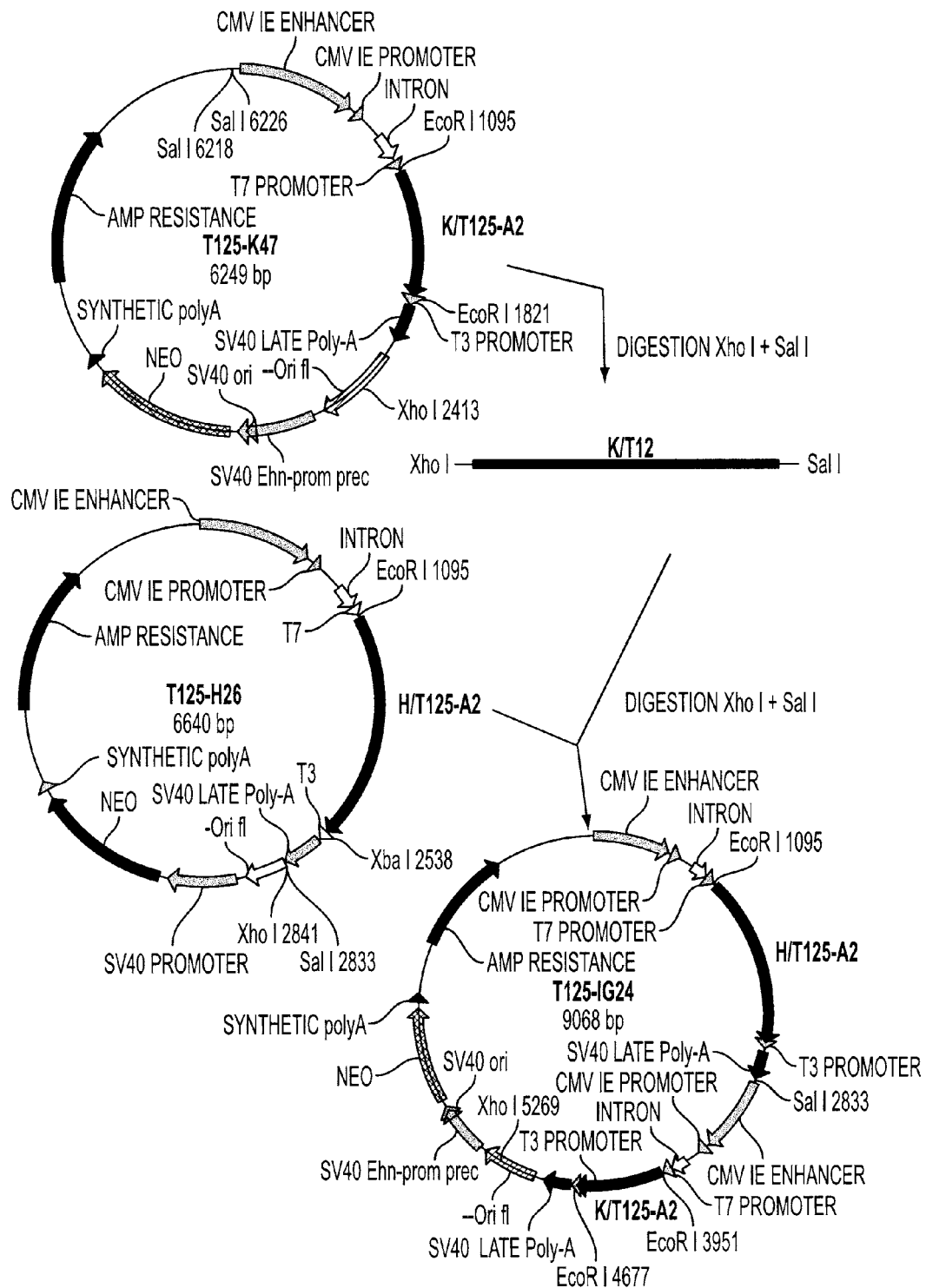
FIG. 5: Construction of the expression vector T125-IG24 for expressing the whole antibody T125

The construction of T125-K47 is given in FIG. 4. The K/T125-A2 sequence obtained by PCR is digested with Eco RI and inserted at the Eco RI site of the expression vector V47 derived from pCI-neo (FIG. 5).

2.3—T125-A2 Heavy and Light Chain Vector: T125-IG24

Figure 6:
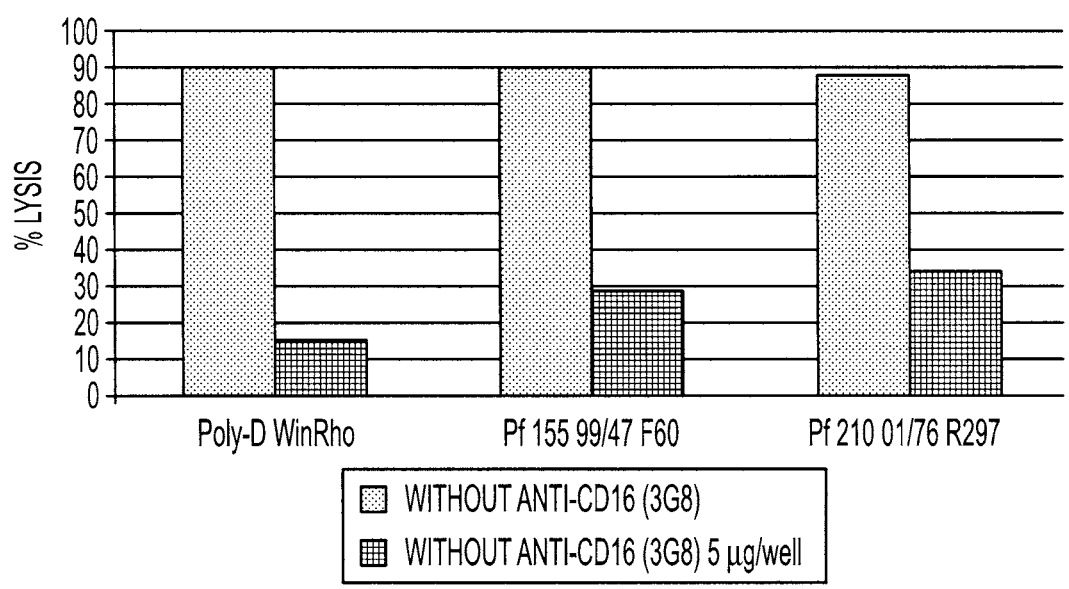
FIG. 6: ADCC inhibition in the presence of anti-FcRIII (CD16)

The construction of T125-IG24 is illustrated diagrammatically in FIG. 6. This vector, which contains the two transcription units for the heavy and Kappa chains of T125-A2, is obtained by inserting the Sal I-Xho I fragment of T125-K47, containing the transcription unit for K/T125-A2, at the Xho I and Sal I sites of T125-H26.

Thus, the heavy and light chains of T125-A2 are expressed under the control of the CMV promoter; other promoters may be used: RSV, IgG heavy chain promoter, MMLV LTR, HIV, β-actin, etc.

2.4—T125-A2 Heavy and Light Chain Specific Leader Vector: T125-LS4

A second vector for expressing T125-A2 is also constructed, in which the consensus leader sequence of the Kappa chain is replaced with the real sequence of the leader region of T125-A2 determined beforehand by sequencing products from "PCR 5'-RACE" (Rapid Amplification of cDNA 5' Ends).

The construction of this T125-LS4 vector is described in FIG. 7. It is carried out in two stages: first of all, construction of a new vector for expressing the T125-A2 Kappa chain, T125-KLS18, and then assembly of the final expression vector, T125-LS4, containing the two heavy chain and modified light chain transcription units.

2.4.1—Construction of the Vector T125-KLS18

The 5' portion of the Kappa consensus leader sequence of the vector T125-K47 is replaced with the specific leader sequence of T125 (KLS/T125-A2) during a step of amplification of the K/T125-A2 sequence carried out using the following primers:

primer A2VK9, modifies the 5' portion of the leader region (in bold) and introduces an Eco RI site (underlined) and also a Kozak sequence (in italics):

A2VK9:
5'-CCTAC<u>GAATTC</u>GCCGCCACC*ATG*AGGGTCCCCGCTCAGCTC-3' primer KSE1 (described in paragraph 1.4)

The vector T125-KLS18 is then obtained by replacing the Eco RI fragment of T125-K47, containing the K/T125-A2 sequence of origin, with the new sequence KLS/T125-A2 digested via Eco RI.

2.4.2—Construction of the Final Vector T125-LS4

The Sal I-Xho I fragment of T125-KLS18, containing the modified KLS/T125-A2 sequence, is inserted into T125-H26 at the Xho I and Sal I sites.

3—Production of Anti-D Abs in the YB2/0 Line 3.1—Without Gene Amplification

The two expression vectors T125-IG24 and T125-LS4 were used to transfect cells of the YB2/0 line (rat myeloma, ATCC line No. 1662). After transfection by electroporation and selection of transformants in the presence of G418 (neo selection), several clones were isolated. The production of recombinant anti-D Abs is approximately 0.2 µg/$10^6$ cells/24 h (value obtained for clone 3B2 of R270). The ADCC activity of this recombinant Ab is greater than or equal to that of the poly-D controls (FIG. 1). The Abs produced using the two expression vectors are not significantly different in terms of level of production or of ADCC activity.

3.2—With Gene Amplification

The gene amplification system used is based on the selection of transformants resistant to methotrexate (MTX). It requires the prior introduction of a transcription unit encoding the DHFR (dihydrofolate reductase) enzyme into the vector for expressing the recombinant Ab (SHITARI et al., 1994).

3.2.1—Construction of the Expression Vector T125-dhfr 13

The scheme shown in FIG. 8 describes the construction of the vector for expressing T125-A2, containing the murine dhfr gene.

A first vector (V64) was constructed from a vector derived from pCI-neo, V43 (FIG. 9), by replacing, 3' of the SV40 promoter and 5' of a synthetic polyadenylation sequence, the neo gene (Hind III-Csp 45 I fragment) with the cDNA of the murine dhfr gene (obtained by amplification from the plasmid pMT2). This vector is then modified so as to create a Cla I site 5' of the dhfr transcription unit. The Cla I fragment containing the dhfr transcription unit is then inserted at the Cla I site of T125-LS4.

3.2.2—Selection in the Presence of MTX

1st Strategy:

YB2/0 cells transfected by electroporation with the vector T125-dhfr13 are selected in the presence of G418. The recombinant Ab-producing transformants are then subjected to selection in the presence of increasing doses of MTX (from 25 nM to 25 µM). The progression of the recombinant Ab production, reflecting the gene amplification process, is followed during the MTX selection steps. The MTX-resistant transformants are then cloned by limiting dilution. The level and the stability of the recombinant Ab production are evaluated for each clone obtained. The anti-D antibody productivity after gene amplification is approximately 13 (+/−7) µg/$10^6$ cells/24 h.

2nd Strategy:

YB2/0 cells transfected by electroporation with vector T125-dhfr13 are selected in the presence of G418. The best recombinant Ab-producing transformants are cloned by limiting dilution before selection in the presence of increasing doses of MTX. The progression of the production by each clone, reflecting the gene amplification process, is followed during the MTX selection steps. The level and the stability of the recombinant Ab production are evaluated for each MTX-resistant clone obtained.

4—Evaluation of the Activity of the T125 Antibody Expressed in YB2/0

After purification by affinity chromatography on protein A Sepharose (Pharmacia) and dialysis into 25 mM Tris buffer, 150 mM NaCl, pH 7.4, the concentration of the T125 antibody is determined by the ELISA technique. The biological activity in vitro is then measured by the ADCC assay described above. The results are given in FIG. 1.

Example 3

Demonstration of the Relationship Between Glycan Structure and FcγRIII-Dependent Activity 1—Cell Culture in the Presence of Deoxymannojirimycin (DMM)

Several studies describe the effect of enzymatic inhibitors on the glycosylation of immunoglobulins and on their biological activity. An increase in ADCC activity is reported by ROTHMAN et al., 1989, this being an increase which cannot be attributed to an enhancement of the affinity of the antibody for its target. The modification of glycosylation caused by adding DMM consists of inhibition of the α-1,2 mannosidase I present in le Golgi. It leads to the production of a greater proportion of polymannosylated, nonfucosylated structures.

Various anti-Rh(D) antibody-producing lines were brought into contact with DMM and the functional activity of the monoclonal antibodies produced was evaluated in the form of culture supernatants or after purification.

The cells (heterohybrid or lymphoblastoid cells) are seeded at between 1 and $3 \times 10^5$ cell/ml, and cultured in IMDM culture medium (Life Technologies) with 10% of FCS and in the presence of 20 μg/ml of DMM (Sigma, Boehringer). After having renewed the medium 3 times, the culture supernatants are assayed by human IgG ELISA and then by ADCC.

TABLE 2

Effect of culturing in the presence of DMM on the ADCC activity of various anti-Rh(D)s

| Samples | ADCC activity as % of the activity of poly-D LFB51 | | Minimum dose of DMM necessary μg/ml |
|---|---|---|---|
| | Culture without DMM | Culture in the presence of DMM | |
| F60 | 109 | 113 | NT |
| D31 | 19 | 87 | 10 |
| DF5 | 26 | 62 | 20 |
| T125 RI(3) | 3 | 72 | 20 |
| T125-CHO | 0 | 105 | 5 |

NT—not tested

Culturing in the presence of deoxymannojirimycin (DMM) brings a significant improvement to the ADCC results for the antibodies previously weakly active, produced by:

| | |
|---|---|
| a human-mouse hybridoma | D31 |
| a human lymphoblastoid line | DF5 |
| a transfected murine line | T125 in CHO |

The addition of DMM may make it possible to restore the ADCC activity of an antibody derived from the cloid T125=T125 RI(3) (described in example 1) and which has lost this activity through sustained culturing.

The strong activity of the antibody produced by the heterohybridoma F60 (the production of which is described in example 1) is not modified by culturing in the presence of DMM.

2—Production of Recombinant Anti-D Antibodies by Various Cell Lines:

2.1—Preparation of an Expression Vector for the Antibody DF5:

The nucleotide sequence of the antibody DF5, a negative control in the ADCC assay, is used to study the transfection of this antibody into some lines, in parallel to transfection of the antibody T125.

The sequences encoding the Ab DF5 are isolated and amplified according to the same techniques used for the recombinant Ab T125-A2.

The corresponding cDNAs are first of all synthesized from total RNA extracted from the anti-D Ab-(IgG G1/Lambda)-producing clone 2MDF5 obtained by EBV transformation.

Amplification of the heavy and light chains is then carried out from these cDNAs using the primers presented below.

Amplification of the variable region of the heavy chain of DF5 (VH/DF5 sequence):

primer DF5VH1, located 5' of the leader region (in bold) of the VH gene of DF5 (sequence published: L. Chouchane et al.); this primer also comprises an Eco RI restriction site (in italics) and a Kozak sequence (underlined):

DF5VH1 (SEQ ID No. 8):
5'CTCTCC*GAATTC*GCCGCCACCATGGACTGGACCTGGAGGATCCTCTT

TTTGGTGG-3' antisense primer GSP2ANP, located 5' of the constant region (CH) already described in paragraph 1.2 (example 2).

Amplification of the constant region CH of DF5 (CH/DF5 sequence): primers G1 and H3'Xba already described in paragraph 1.3 (example 2).

Amplification of the Lambda light chain of DF5 (LBD/DF5 sequence):

primer DF5VLBD1, located 5' of the leader region of the VL gene of DF5, introduces a consensus sequence (in bold) deduced from the sequence of several leader regions of VL genes belonging to the same VL1 subgroup as the VL gene of 2MDF5; this sequence also comprises an Eco RI restriction site (in italics) and a Kozak sequence (underlined):

DF5VLBD1 (SEQ ID No. 9):
5'CCTACC*GAATTC*GCCGCCACCATGGCCTGGTCTCCTCTCCTCCTC

AC-3' antisense primer LSE1, located 3' of Lambda, introduces an Eco RI site (underlined):

LSE1 (SEQ ID No. 10):
5'-GAGGAGGAATTCACTATGAACATTCTGTAGGGGCCACTGTCTT-3'.

The construction of the vectors for expressing the heavy chain (DF5-H31), light chain (DF5-L10) and heavy and light chains (DF5-IG1) of the Ab DF5 is carried out according to a construction scheme similar to vectors expressing the Ab T125-A2. All the leader sequences of origin (introduced in the amplification primers) are conserved in these various vectors.

2.2—Transfection of Various Cell Lines with the Antibodies T125 and DF5

The three expression vectors T125-IG24, T125-LS4 and DF5-IgG1 are used to transfect cells of various lines: Stable or transient transfections are performed by electroporation or using a transfection reagent.

TABLE 3

Cell lines used for the transfection of anti-Rh(D) antibodies

| Name | Reference | Cell type |
|---|---|---|
| CHO-K1 | ATCC CCL 61 | Chinese hamster ovary (epithelium like) |
| CHO-Lec10 | Fenouillet et al., 1996, Virology, 218, 224-231 | Chinese hamster ovary (epithelium like) |
| Jurkat | ATCC TIB-152 | Human T lymphocyte (T leukemia) |
| Molt-4 | ATCC CRL 1582 | Human T lymphocyte (acute lymphoblastic leukemia) |
| WIL2-NS | ATCC CRL 8155 | EBV-transformed human B lymphocyte |
| Vero | ATCC CCL 81 | African green monkey kidney (fibroblast like) |
| COS-7 | ATCC CRL 1651 | SV40-transformed African green monkey kidney (fibroblast like) |
| 293-HEK | ATCC CRL 1573 | Primary human embryonic kidney transformed with defective adenovirus 5 DNA |
| YB2/0 | ATCC CRL 1662 | Nonsecreting rat myeloma |
| BHK-21 | ATCC CCL 10 | Newborn hamster kidney (fibroblast like) |
| K6H6-B5 | ATCC CRL 1823 | Nonsecreting human-mouse heteromyeloma |
| NSO | ECACC 85110503 | Nonsecreting mouse myeloma (lymphoblast like) |
| SP2/0-Ag 14 | ECACC 85072401 | Nonsecreting mouse × mouse hybridoma |
| CHO Lec-1 | ATCC CRL 1735 | Chinese hamster ovary |
| CHO dhfr | ECACC 94060607 | Chinese hamster ovary |
| CHO Pro-5 | ATCC CRL 1781 | Chinese hamster ovary |
| P3X63 Ag8.653 | ATCC CRL 1580 | Nonsecreting mouse myeloma |

After selection of the transformants in the presence of G418 (neo selection), several clones were isolated.

The modification of effector activity of a humanized monoclonal antibody as a function of the expressing cell has been described by CROWE et al. (1992), with the CHO, NSO and YB2/0 cell lines.

The results obtained here confirm the importance of the expressing cell line with respect to the functional characteristics of the antibody to be produced. Among the cells tested, only the Vero, YB2/0 and CHO Lec-1 lines make it possible to express recombinant anti-Rh(D) monoclonal antibodies with strong lytic activity in the ADCC assay (see example 1 and table 4).

3—Study of the Glycan Structures

Characterization of the glycan structures of the anti-Rh-D antibody was carried out on four purified products having an ADCC activity (F60, and three recombinant proteins derived from T125) in comparison with two purified products inactive or very weakly active in the ADCC assay according to the invention (D31 and DF5).

In practice, the oligosaccharides are separated from the protein by specific enzymatic deglycosylation with PNGase F at Asn 297. The oligosaccharides thus released are labeled with a fluorophore, separated and identified by various complementary techniques which allow:

fine characterization of the glycan structures by matrix-assisted laser desorption ionization (MALDI) mass spectrometry by comparison of the experimental masses with the theoretical masses.

determination of the degree of sialylation by ion exchange HPLC (GlycoSep C)

separation and quantification of the oligosacharride forms according to hydrophilicity criteria by normal-phase HPLC (GlycoSep N)

separation and quantification of the oligosaccharides by high performance capillary electrophoresis-laser induced fluorescence (HPCE-LIF).

1) Characterization of the Glycans of Active Forms

The various active forms studied are F60 and three recombinant antibodies, R 290, R 297 and R 270, derived from T125 and produced in YB2/0. Fine characterization of the glycan structures by mass spectrometry (FIG. 7) shows that these forms are all of the bi-antennary type. In the case of R 270, the major form is of the agalactosylated, nonfucosylated type (G0, exp. mass 1459.37 Da, FIG. 1). Three other structures are identified: agalactosylated, fucosylated (G0F at 1605.41 Da), monogalactosylated, nonfucosylated (G1 at 1621.26 Da) and monogalactosylated, fucosylated (G1F at 1767.43 Da) in minor amount. These same four structures are characteristic of R 290, F 60 and R 297 (FIG. 1).

These four antibodies which are active in ADCC are also characterized by the absence of oligosaccharides having a bisecting N-acetylglucosamine residue.

Quantification of the glycan structures by the various techniques of HPLC and HPCE-LIF (table 1) confirms the presence of the four forms identified by mass: G0, G0F, G1 and

TABLE 4

ADCC activity of the antibodies DF5 and T125 obtained by transfection into various cell lines. The results are expressed as percentage of the activity of the reference polyclonal antibody: Poly-D LFB 51

| | | Transfected cell lines | | | | | | | | |
|---|---|---|---|---|---|---|---|---|---|---|
| | | CHO-K1 | CHO-Lec10 | Wil-2 | Jurkat | Vero | Molt-4 | COS-7 | 293-HEK | YB2/0 |
| antibodies | T125 | 7 +/− 8  n = 13 | 22 +/− 6  n = 11 | 3 +/− 5  n = 12 | 6 +/− 8  n = 7 | 90 +/− 21  n = 5 | 0  n = 1 | 13 +/− 2  n = 4 | 16 +/− 13  n = 12 | 114 +/− 28  n = 54 |
| | DF5 | NT | 51 +/− 19  n = 3 | NT | NT | 72 +/− 17  n = 5 | NT | 21 +/− 4  n = 4 | 12 +/− 14  n = 12 | 94 +/− 15  n = 15 |

| | | Transfected cell lines | | | | | | | |
|---|---|---|---|---|---|---|---|---|---|
| | | NSO | BHK | CHO-Lec1 | SP2/0-Ag14 | K6H6-B5 | CHO Pro-5 | CHO dhfr | P3X63A g8.653 |
| antibodies | T125 | 6 +/− 8  n = 3 | 13 +/− 5  n = 4 | 106 +/− 60  n = 4 | 0 +/− 0  n = 6 | 9 +/− 8  n = 3 | 3 +/− 3  n = 4 | 13 +/− 8  n = 12 | 34 +/− 8  n = 9 |

G1F. The degree of sialylation is very low, in particular for the recombinant products, from 1 to 9.4%, which is confirmed by the similarity of the mass spectra obtained before and after enzymatic desilylation. The degree of fucosylation ranges from 34 to 59%.

2) Inactive Forms

The various inactive forms studied are D31 and DF5. Quantification of the glycan structures by the various chromatographic and capillary electrophoresis techniques (table 1) reveals, for these two antibodies, a degree of sialylation close to 50%, and a degree of fucosylation of 88 and 100% for D31 and DF5, respectively. These degrees of sialylation and fucosylation are much higher than those obtained from the active forms.

Characterization of the glycan structures shows that the major form is, for the two antibodies, of the bi-antennary, monosialylated, digalactosylated, fucosylated type (G2S1F, table 1). The characterization by mass spectrometry of D31 (FIG. 7) reveals that the neutral forms are mainly of the monogalactosylated, fucosylated type (G1F at 1767.43 Da) and digalactosylated, fucosylated type (G2F at 1929.66 Da).

The inactive antibody DF5 is characterized by the presence of oligosaccharides having an intercalated GlcNAc residue. In particular, the mass analysis (FIG. 8) reveals the presence of a major neutral form of the monogalactosylated, fucosylated, bisecting, intercalated GlcNAc type (G1FB at 1851.03 Da). On the other hand, these structural forms are undetectable or present in trace amounts on the active antibodies studied.

The ADCC activity of D31 after the action of DMM increases from 10% to 60%. The glycan structures of DMM D31 differ from those of D31 by the presence of oligomannose forms (Man 5, Man 6 and Man 7) (see FIG. 9).

3) Conclusion

The various active antibodies are modified on Asn 297 with N-glycosylations of the bi-antennary and/or oligomannoside type. For the bi-antennary forms, this involves short structures with a very low degree of sialylation, a low degree of fucosylation, a low degree of galactosylation and no intercalated GlcNAc.

REFERENCES

Boylston, J. M., Gardner, B., Anderson, R. L., and Hughes-Jones, N. C. Production of human IgM anti-D in tissue culture by EB virus-transformed lymphocytes. Scand. J. Immunol. 12: 355-358 (1980).

Bron, D., Feinberg, M. B., Teng, N. N. H. and Kaplan, H. S. Production of Human Monoclonal IgG Antibodies against Rhesus (D) Antigen. Proc. Nat. Acad. Sci. USA 81: 3214-3217 (1984).

Chouchane, L., Van Spronsen, A., Breyer, J., Guglielmi, P., and Strosberg, A D. Molecular characterization of a human anti-Rh(D) antibody with a DII segment encoded by a germ-line sequence. Eur. J. Biochem. 1; 207(3): 1115-1121 (1992).

Crawford, D. H., Barlow, M. J., Harrison, J. F., Winger, L. and Huehns, E. R. Production of human monoclonal antibody to rhesus D antigen. Lancet, i: 386-388 (1983).

Doyle, A., Jones, T. J., Bidwell, J. L. and Bradley, B. A. In vitro development of human monoclonal antibody secreting plasmacytomas. Hum. Immunol. 13: 199-209 (1985).

Edelman, L., Margarine, C., Chaabihi, H., Monchâtre, E., Blanchard, D., Cardona, A., Morin, F., Dumas, G., Petres, S. and Kaczorek, M. Obtaining a functional recombinant anti-rhesus (D) antibody using the baculovirus-insect cell expression System. Immunology, Vol. 91(1), 13-19 (1997).

Foung, S. K. H., Blunt, J. A., Wu, P. S., Ahearn, P., Winn, L. C., Engleman, E. G. and Grumet, F. C. Human Monoclonal Antibodies to Rho (D). Vox Sang. 53: 44-47 (1987).

Goossens, D., Champomier, F., Rouger, P., and Salmon, C. Human Monoclonal Antibodies against Blood Group Antigens: Preparation of a series of stable EBV immortalized B clones producing high levels of antibody of different isotypes and specificities. J. Immunol. Methods 101: 193-200 (1987).

Issitt, P. D. Genetics of the Rh Blood Group System: Some Current Concepts. Med. Lab. Sci. 45: 395-404 (1988).

Jefferis, R, Lund, J., Mizutani, H., Nakagawa, H., Kawazoe, Y., Arata, Y. and Takahashi, N. A comparative study of the N-linked oligosaccharides structure of human IgG Subclass proteins. Biochem. J., 268: 529-537 (1990).

Koskimies, S. Human Lymphoblastoid Cell Line Producing Specific Antibody against Rh-Antigen D. Scand. Immunol. 11:73-77 (1980).

Kumpel, B. M., Goodrick, M. J., Pamphilon, D. H., Fraser, I. D., Poole G. D., Morse, C., Standen, G. R., Chapman, G. E., Thomas, D. P. and Anstee, D. J. Human Rh D monoclonal antibodies (BRAD-3 and BRAD-5) Cause Accelerated Clearance of Rh D+ Red blood Cells and Suppression of Rh D Immunization in Rh D Volunteers. Blood, Vol. 86, No. 5, 1701-1709 (1995).

Kumpel, B. M., Poole, G. D. and Bradley, B. A. Human Monoclonal Anti-D Antibodies. I. Their Production, Serology, Quantitation and Potential Use as Blood Grouping Reagents. Brit. J. Haemat. 71: 125-129 (1989a).

Kumpel, B. M., Rademacher, T. W., Rook, G. A. W., Williams, P. J., Wilson, I. B. M. Galacatosylation of human IgG anti-D produced by EBV-transformed B lymphoblastoid cell lines is dependent on culture method and affects Fc receptor mediated functional activity. Hum. Antibodies and Hybridomas, 5: 143-151 (1994).

Leatherbarrow, R. J., Rademacher, T. W., Dwek, R. A., Woof, J. M., Clark, A., Burton, D. R., Richardson, N. and Feinstein, A. Effector functions of monoclonal aglycosylated mouse IgG2a; binding and activation of complement component CI and interaction with human Fc receptor. Molec. Immun. 22, 407-415 (1985).

Lomas, C., Tippett, P., Thompson, K. M., Melamed, M. D. and Hughes-Jones, N. C. Demonstration of seven epitopes on the Rh antigen D using human monoclonal anti-D antibodies and red cells from D categories. Vox Sang. 57: 261-264 (1989).

Lund, J., Takahaski, N., Nakagawa, H., Goodall, M., Bentley, T., Hindley, S. A., Tyler, R. and Jefferis, R. Control of IgG/Fc glycosylation: a comparison of oligosaccharides from chimeric human/mouse and mouse subclass immunoglobulin G5. Molec. Immun. 30, No. 8, 741-748 (1993).

Lund, J., Tanaka, T., Takahashi, N., Sarmay, G., Arata, Y. and Jefferis, R. A protein structural change in aglycosylated IgG3 correlates with loss of hu Fc□RI and Hu FcγRIII binding and/or activation. Molec. Immun. 27, 1145-1153 (1990).

Ma, J. K. and Hein, M. B. Immunotherapeutic potential of antibodies produced in plants. Trends Biotechnol. 13, 522-527 (1995).

Mc Cann-Carter, M. C., Bruce, M., Shaw, E. M., Thorpe, S. J., Sweeney, G. M., Armstrong, S. S. and James, K. The production and evaluation of two human monoclonal anti-D antibodies. Transf. Med. 3: 187-194 (1993).

Melamed. M. D., Gordon, J., Ley, S. J., Edgar, D. and Hughes-Jones, N. C. Senescence of a human lymphoblastoid clone producing anti-Rhesus (D) Eur. J. Immunol. 115: 742-746 (1985).

Parekh, R. B., Dwek, R. A., Sutton, B. J., Fernanes, D. L., Leung, A., Stanworth, D., Rademacher, T. W., Mizuochi, T., Taniguchi, T., Matsuta, K., Takeuchi, F., Nagano, Y., Miyamoto, T. and Kobata, A. Association of rheumatoid arthritis and primary osteoarthritis with changes in the glycosylation pattern of total serum IgG. Nature, 316: 452-457 (1985).

Rothman, R. J., Perussia, B., Herlyn, D. and Warren, L. Antibody-dependent cytotoxicity mediated by natural killer cells is enhanced by castanospermine-induced alterations of IgG glycosylation. Mol. Immunol. 26(12): 1113-1123 (1989).

Shitara K., Nakamura K., Tokutake-Tanaka Y., Fukushima M., and Hanai N. A new vector for the high level expression of chimeric antibodies to myeloma cells. J. Immunol. Methods 167: 271-278 (1994).

Thompson, K. M., Hough, D. W., Maddison, P. J., Mclamed, M. D. and Hughes-Jones, N. C. Production of human monoclonal IgG and IgM antibodies with anti-D (rhesus) specificity using heterohybridomas. Immunology 58: 157-160 (1986).

Thomson, A., Contreras, M., Gorick, B., Kumpel, B., Chapman, G. E., Lane, R. S., Teesdale, P. Hughes-Jones, N. C. and Mollison, P. L. Clearance of Rh D-positive red cells with monoclonal anti-D. Lancet 336: 1147-1150 (1990).

Tippett, P. Sub-divisions of the Rh(D) antigen. Med. Lab. Sci. 45: 88-93 (1988).

Ware, R. E. and Zimmerman, S. A. Anti-D: Mechanisms of action. Seminars in Hematology, vol. 35, No. 1, supp. 1: 14-22 (1998).

Yu, I. P. C., Miller, W. J., Silberklang, M., Mark, G. E., Ellis, R. W., Huang, L., Glushka, J., Van Halbeek, H., Zhu, J. and Alhadeff, J. A. Structural characterization of the N-Glycans of a humanized anti-CD18 murine immunoglobulin G. Arch. Biochem. Biophys. 308, 387-399 (1994).

Zupanska, B., Thompson, E., Brojer, E. and Merry, A. H. Phagocytosis of Erythrocytes Sensitized with Known Amounts of IgG1 and IgG3 anti-Rh antibodies. Vox Sang. 53: 96-101 (1987).

What is claimed is:

1. A cell culture, comprising an isolated clone, wherein said cell culture produces monoclonal antibodies having on the Fcγ glycosylation site (Asn 297, EU numbering) bi-antennary glycan structures, wherein said glycan structures of the monoclonal antibodies have a fucose content less than 65%, and wherein said glycan structures of the monoclonal antibodies have a content greater than 60% for the G0+G1+G0F+G1F forms

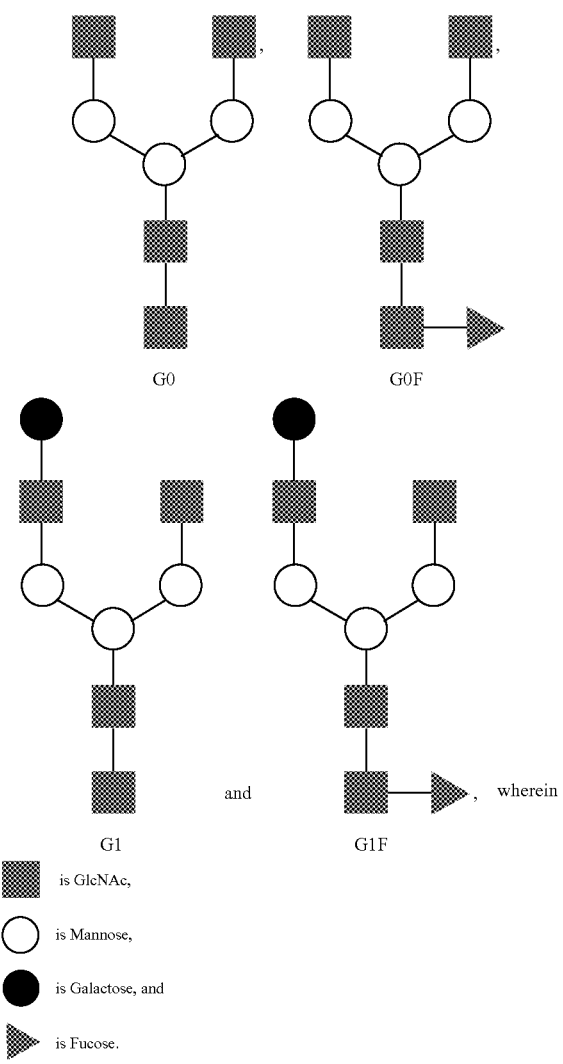

is GlcNAc, is Mannose, is Galactose, and is Fucose.

2. The cell culture of claim 1, wherein the fucose content is less than 30%.

3. The cell culture of claim 1, wherein the fucose content is between 20% and 45%.

4. The cell culture of claim 3, wherein the fucose content is between 25% and 40%.

5. The cell culture of claim 1, wherein the monoclonal antibodies are directed against an antigen, and activate effector cells expressing Fcγ type III receptors, causing a lysis of target cells presenting the antigen greater than 60% of a lysis caused by polyclonal antibodies directed against the antigen.

6. The cell culture of claim 5, wherein the antigen is rhesus D.

7. The cell culture of claim 1, wherein the monoclonal antibodies are directed against an antigen, and activate effector cells expressing Fcγ type III receptors, causing a lysis of target cells presenting the antigen greater than 90% of a lysis caused by polyclonal antibodies directed against the antigen.

8. The cell culture of claim 7, wherein the antigen is rhesus D.

9. The cell culture of claim 1, wherein the monoclonal antibodies are IgG1 antibodies.

10. The cell culture of claim 1, wherein the monoclonal antibodies are IgG3 antibodies.

11. The cell culture of claim 1, wherein said glycan structures of the monoclonal antibodies have a sialic acid content of less than 25%.

12. A cell culture, comprising an isolated clone, wherein said cell culture produces monoclonal antibodies having on the Fcγ glycosylation site (Asn 297, EU numbering) bi-antennary glycan structures,
wherein said glycan structures of the monoclonal antibodies have a content less than 50% for the G0F+G1F forms, and
wherein said glycan structures of the monoclonal antibodies have a content greater than 60% for the G0+G1+G0F+G1F forms.

13. The cell culture of claim 12, wherein said glycan structures of the monoclonal antibodies have a content less than 30% for the G0F+G1F forms.

14. The cell culture of claim 12, wherein said glycan structures of the monoclonal antibodies have a content greater than 80% for the G0+G1+G0F+G1F forms.

15. The cell culture of claim 12, wherein the monoclonal antibodies are directed against an antigen, and activate effector cells expressing Fc type III receptors, causing a lysis of target cells presenting the antigen greater than 60% of a lysis caused by polyclonal antibodies directed against the antigen.

16. The cell culture of claim 15, wherein the monoclonal antibodies cause a lysis of target cells presenting the antigen greater than 70% of a lysis caused by polyclonal antibodies directed against the antigen.

17. The cell culture of claim 16, wherein the monoclonal antibodies cause a lysis of target cells presenting the antigen greater than 80% of a lysis caused by polyclonal antibodies directed against the antigen.

18. The cell culture of claim 17, wherein the monoclonal antibodies cause a lysis of target cells presenting the antigen greater than 90% of a lysis caused by polyclonal antibodies directed against the antigen.

19. The cell culture of claim 12, wherein said monoclonal antibodies are IgG1 antibodies.

20. The cell culture of claim 12, wherein said monoclonal antibodies are IgG3 antibodies.

21. The cell culture of claim 12, wherein said monoclonal antibodies are anti Rh(D) antibodies.

22. The cell culture of claim 12, wherein said glycan structures of the monoclonal antibodies have a sialic acid content of less than 25%.

23. The cell culture of claim 1, wherein the isolated clone is produced by transfection of the cell line deposited with the ATCC as accession number CRL-1662.

24. The cell culture of claim 12, wherein the isolated clone is produced by transfection of the cell line deposited with the ATCC as accession number CRL-1662.

25. The cell culture of claim 1, wherein the isolated clone is isolated from a cell line transfected with a gene coding for said monoclonal antibodies.

26. The cell culture of claim 12, wherein the isolated clone is isolated from a cell line transfected with a gene coding for said monoclonal antibodies.

* * * * *